(12) United States Patent
Harano et al.

(10) Patent No.: US 7,001,381 B2
(45) Date of Patent: Feb. 21, 2006

(54) ELECTRIC OPERATION APPARATUS

(75) Inventors: Kenji Harano, Hachioji (JP);
Masahide Ohyama, Hino (JP); Kazuya Hijii, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/634,449

(22) Filed: Nov. 17, 2003

(65) Prior Publication Data

US 2005/0101949 A1   May 12, 2005

Related U.S. Application Data

(63) Continuation of application No. 09/727,876, filed on Dec. 1, 2000, now Pat. No. 6,635,057.

(30) Foreign Application Priority Data

Dec. 2, 1999   (JP)   ............................... H11-343691
Dec. 24, 1999  (JP)   ............................... H11-368189

(51) Int. Cl.
*A61B 18/12*   (2006.01)

(52) U.S. Cl. ..................... 606/40; 128/898; 606/49; 606/50

(58) Field of Classification Search ............ 606/38–50; 128/898
See application file for complete search history.

(56) References Cited

U.S. PATENT DOCUMENTS

| | | |
|---|---|---|
| 4,094,320 A | 6/1978 | Newton et al. |
| 4,658,819 A | 4/1987 | Harris et al. |
| 4,727,874 A | 3/1988 | Bowers et al. |
| 5,437,662 A | 8/1995 | Nardella |
| 5,456,682 A | 10/1995 | Edwards et al. |
| 5,496,312 A | 3/1996 | Klicek |
| 5,558,671 A | 9/1996 | Yates |
| 5,720,744 A | 2/1998 | Eggleston et al. |
| 5,733,281 A * | 3/1998 | Nardella ...................... 606/38 |
| 5,735,846 A * | 4/1998 | Panescu et al. ............... 606/41 |
| 5,931,836 A | 8/1999 | Hatta et al. |
| 6,033,399 A | 3/2000 | Gines |
| 6,083,223 A * | 7/2000 | Baker .......................... 606/52 |
| 6,183,468 B1 | 2/2001 | Swanson et al. |
| 6,203,541 B1 | 3/2001 | Keppel |
| 6,210,403 B1 | 4/2001 | Klicek |
| 6,306,131 B1 | 10/2001 | Hareyama et al. |
| 6,398,779 B1 * | 6/2002 | Buysse et al. ................ 606/34 |
| 6,436,096 B1 | 8/2002 | Hareyama |
| 6,635,057 B1 * | 10/2003 | Harano et al. ................ 606/40 |

FOREIGN PATENT DOCUMENTS

DE   3904558 A1   8/1990

(Continued)

*Primary Examiner*—Henry M Johnson, III
(74) *Attorney, Agent, or Firm*—Scully, Scott, Murphy & Presser

(57) ABSTRACT

An electric operation apparatus including: a high frequency current generating circuit for feeding a high frequency current to electrodes; a direct power supply circuit for supplying variable electric power to the high frequency current generating circuit; a therapeutic condition monitoring circuit for monitoring a therapeutic condition brought about by the high frequency current on the basis of the high frequency current outputted by the high frequency electric current generating circuit; and a supplied power setting circuit for supplying a setting signal for supplied electric power to the power supply circuit on the basis of the monitoring results obtained by the therapeutic condition monitoring circuit.

28 Claims, 17 Drawing Sheets

FOREIGN PATENT DOCUMENTS

| | | |
|---|---|---|
| DE | 4233467 A1 | 4/1994 |
| JP | H8-98845 | 4/1996 |
| JP | 08196543 A | 8/1996 |
| JP | H10-225462 | 8/1998 |

* cited by examiner

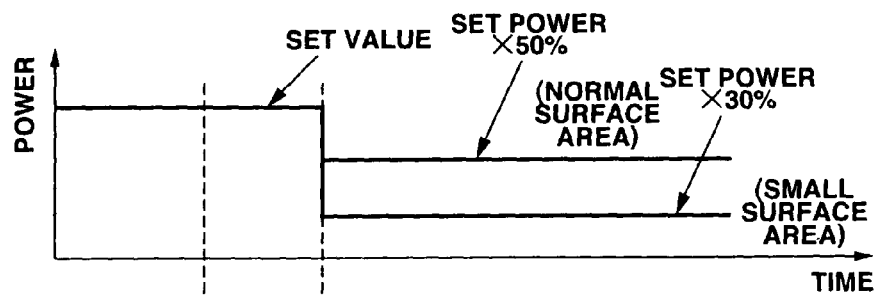
FIG.11A
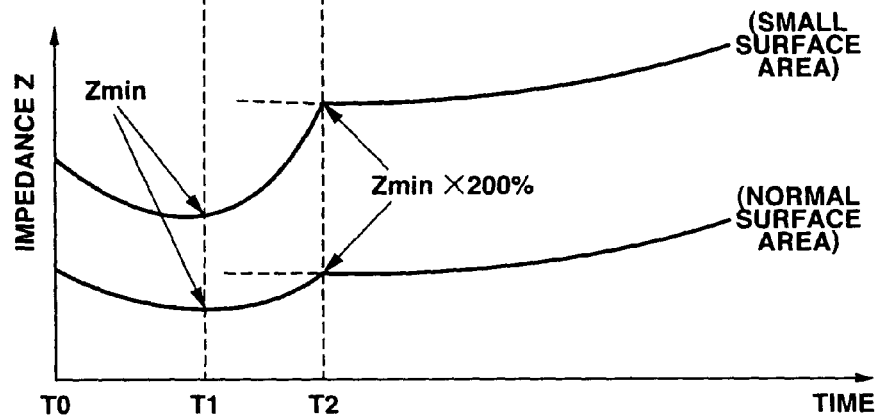
FIG.11B
FIG.12
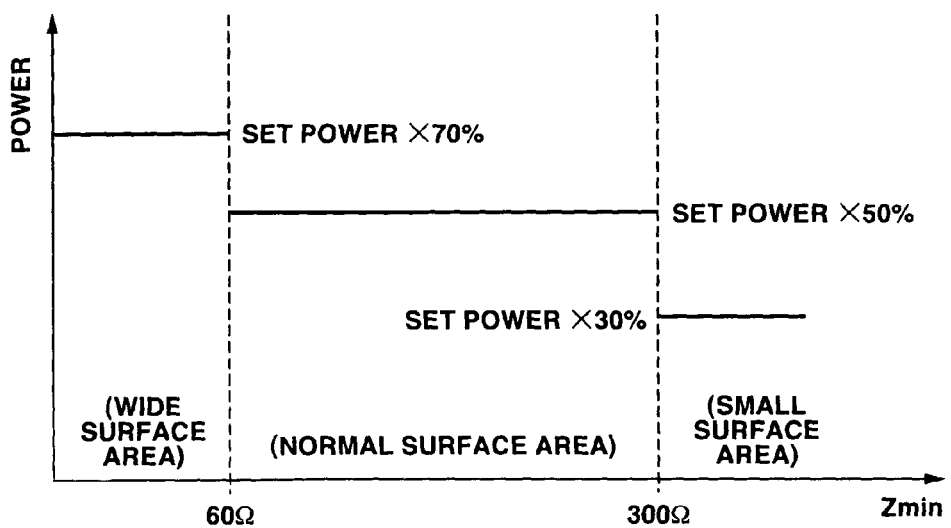

ELECTRIC OPERATION APPARATUS

This is a continuation of application Ser. No. 09/727,876 filed on Dec. 1, 2000, now U.S. Pat. No. 6,635,057.

This application claims benefit of Japanese Applications No. H11-343691 filed in Japan on Dec. 2, 1999 and No. H11-368189 filed on Dec. 24, 1999, the contents of which are incorporated by this reference.

BACKGROUND OF THE INVENTION

1. Field of the Invention

The present invention relates to an electric operation apparatus, and more particularly to an electric operation apparatus and an output control method featuring a specific output control section for high frequency current.

2. Description of the Related Art

Electric knives and other types of electric operation apparatus are commonly used to incise or coagulate biological tissue, to stop bleeding, or to perform other procedures when internal or external surgery is conducted.

Such an electric operation apparatus comprises a high frequency cauterizing power supply unit and a treatment means connected to the high frequency cauterizing power supply unit, with the aforementioned treatment being performed by the application of the treatment means to the patient and feeding high frequency power from the high frequency cauterizing power supply unit.

Various proposals have been made concerning the aforementioned electric operation apparatus. For example, Japanese Patent Laid-open No. H8-98845 discloses a technique in which coagulation completion is verified on the basis of tissue impedance, and high frequency output is stopped in order to prevent the coagulating tissue from carbonizing and adhering to electrodes.

A technique for reducing the high frequency output in order to achieve the same object as in Japanese Patent Laid-open No. H8-98845 is also disclosed in connection with the electric operation apparatus described in Japanese Patent Laid-open No. H10-225462.

It should be noted that tissue impedance varies more rapidly with a reduction in the contact area between the tissue and the electrodes.

The electric operation apparatus described in Japanese Patent Laid-open Nos. H8-98845 and H10-225462 are configured such that, in case a narrow contact area is formed between the tissue and the electrodes, the tissue, sometimes, carbonizes or adheres to the electrodes while tissue impedance is measured or coagulation completion is verified.

Japanese Patent Laid-open No. H10-225462 discloses a technique in which the output of a high frequency current is reduced without being stopped after coagulation completion has been verified. According to this technique, a treatment can be continued if a surgeon or other specialist determines that insufficient coagulation has been achieved following verification of coagulation made by an electric operation apparatus. In the process, tissue degeneration can be slowed down due to reduced high frequency output, and the specialist can terminate the treatment once the desired coagulation state has been achieved.

However, the small size of the contact area between the tissue and the electrodes speeds up tissue degeneration and makes it more difficult for a specialist to terminate treatment once the desired coagulation state has been achieved. Another drawback is that a large contact area results in excessively slow tissue degeneration, and takes too long to obtain the desired coagulation state.

Yet another feature is that reducing the contact area between the tissue and the electrodes tends to make impedance, electric current, and the like susceptible to the influence of electrode operation and the like, and allows these parameters to be affected by factors unrelated to the coagulation state of the tissue.

The electric operation apparatus disclosed in Japanese Patent Laid-open Nos. H8-98845 and H10-225462 are disadvantageous in that when a small contact area is formed between the tissue and the electrodes, measurement results concerning electric current and the like become unstable and coagulation is sometimes considered to be complete even though in reality it is not.

SUMMARY OF THE INVENTION

An object of the present invention, which was accomplished in view of the above-described situation, is to provide an electric operation apparatus and an output control method that make it possible to consistently verify coagulation completion and to prevent tissue from carbonizing or adhering to electrodes irrespective of the size of the contact area between the tissue and the electrodes.

Another object of the present invention is to provide an electric operation apparatus and an output control method that allow the tissue degeneration rate to be kept within a range readily discernible by the specialist and the coagulation state to be easily identifiable irrespective of the size of the contact area between the tissue and the electrodes.

Yet another object of the present invention is to provide an electric operation apparatus and an output control method that prevent tissue from carbonizing or adhering to electrodes and that allow coagulation and other types of therapeutic treatments to be consistently performed even with a variable contact area.

Aimed at attaining the stated objects, the electric operation apparatus of the present invention comprises a high frequency current generating circuit for generating high frequency current and feeding this high frequency current to electrodes, and a direct current power supply circuit for feeding power to the high frequency generating circuit. With the direct current power supply circuit, the power being fed is variable. The electric operation apparatus also has a therapeutic condition monitoring circuit for monitoring the therapeutic condition induced by the high frequency current on the basis of the high frequency current outputted by the high frequency current generating circuit, and a supplied power setting circuit for feeding a setting signal for the power supply to the direct current power supply circuit on the basis of the monitoring results obtained by the therapeutic condition monitoring circuit.

The inventive output control method for an electric operation apparatus involves using an electric operation apparatus comprising a high frequency current generating circuit for generating high frequency current and feeding this high frequency current to electrodes, and a direct current power supply circuit for feeding power to the high frequency generating circuit, wherein the direct current power supply circuit is such that the power being fed is variable. In addition, the therapeutic condition induced by the high frequency current is monitored on the basis of the high frequency current outputted by the high frequency current generating circuit, and a setting signal for the power supply is fed to the direct current power supply circuit on the basis of the monitoring results.

In more specific terms, the therapeutic condition monitoring circuit determines the therapeutic condition by comparing the current high frequency electric current value with a preset threshold value. The supplied power setting circuit compares the high frequency current with a preset target value and changes the setting signal to reduce the power supply to a prescribed level if it is verified based on the comparison results that the coagulation treatment has been completed. The target value is determined based on the maximum value of the high frequency current. The therapeutic condition monitoring circuit also determines the therapeutic condition by using the thickness of tissue between at least two electrodes for transmitting the high frequency current to a subject's tissue. The therapeutic condition monitoring circuit determines the therapeutic condition by comparing the impedance value of the subject being treated with the threshold value established based on thickness. The threshold value is selected based on the minimum value of the impedance value thus measured. The therapeutic condition monitoring circuit determines the therapeutic condition on the basis of the amount of time corresponding to variations in the electric current value sampled. The therapeutic condition monitoring circuit determines the therapeutic condition on the basis of the time needed to achieve the maximum value of the electric current value thus sampled. The supplied power setting circuit compares the current value of the high frequency current with a threshold value established based on the aforementioned maximum value, and changes the setting signal in order to reduce the power supply on the basis of the comparison results. The supplied power setting circuit determines whether the high frequency electric current value has reached a preset threshold value after a predetermined time indicating the end of a blood coagulation treatment has elapsed, and changes the setting signal in order to reduce the power supply if it is established that coagulation has indeed occurred. The therapeutic condition monitoring circuit determines the therapeutic condition on the basis of the amount of time corresponding to variations in the sampled impedance value of the subject being treated. The therapeutic condition monitoring circuit determines the therapeutic condition on the basis of the time needed for the sampled impedance value of the subject being treated to reach its minimum value. The supplied power setting circuit compares the current impedance with a threshold value established based on the aforementioned minimum value, and changes the setting signal in order to reduce the power supply on the basis of the comparison results. The supplied power setting circuit determines whether the impedance value has reached a preset threshold value after a predetermined time indicating the end of a blood coagulation treatment has elapsed, and changes the setting signal in order to reduce the power supply if it is established that coagulation has indeed occurred.

BRIEF DESCRIPTION OF THE DRAWINGS

FIG. 11A is a diagram illustrating a specific example of the manner in which the set value of electric power varies with time when a high frequency current is allowed to flow.

FIG. 11B is a diagram illustrating a specific example of the manner in which the impedance varies with time when a high frequency current is allowed to flow.

FIG. 12 is a diagram illustrating the manner in which the value of electric power is set in accordance with the minimum impedance value;

DESCRIPTION OF THE PREFERRED EMBODIMENTS

Embodiments of the present invention will now be described with reference to the appended drawings.

Figure 1:
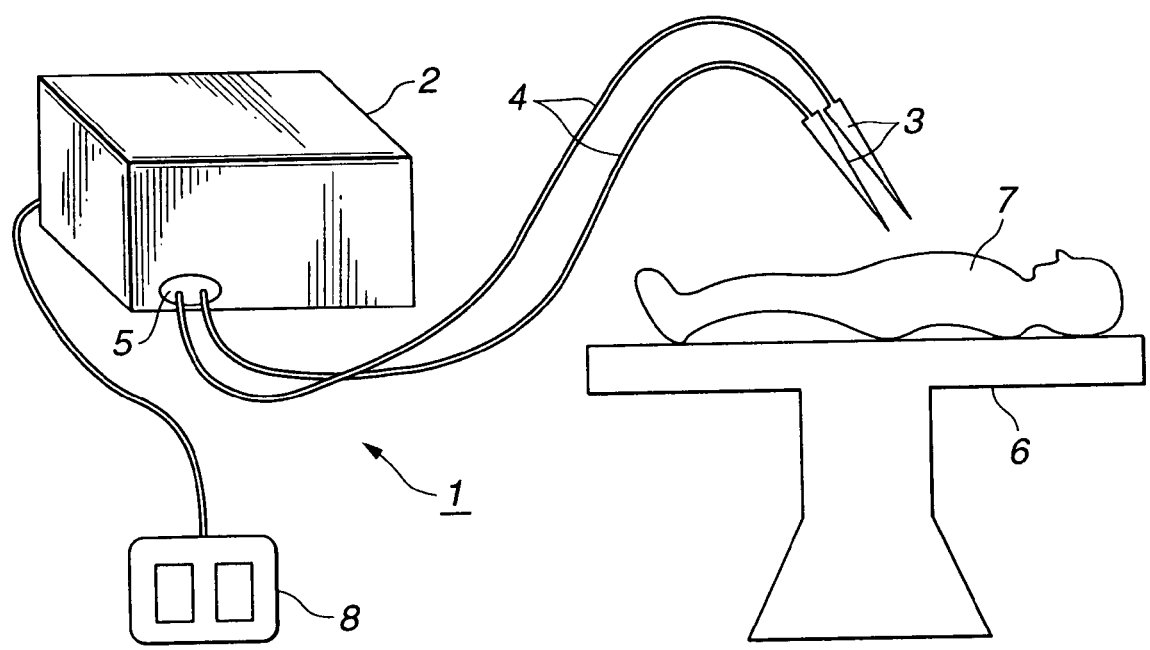
FIG. 1 is a general layout of a high frequency cauterizing unit pertaining to a first embodiment of the inventive electric operation apparatus.
Figure 2:
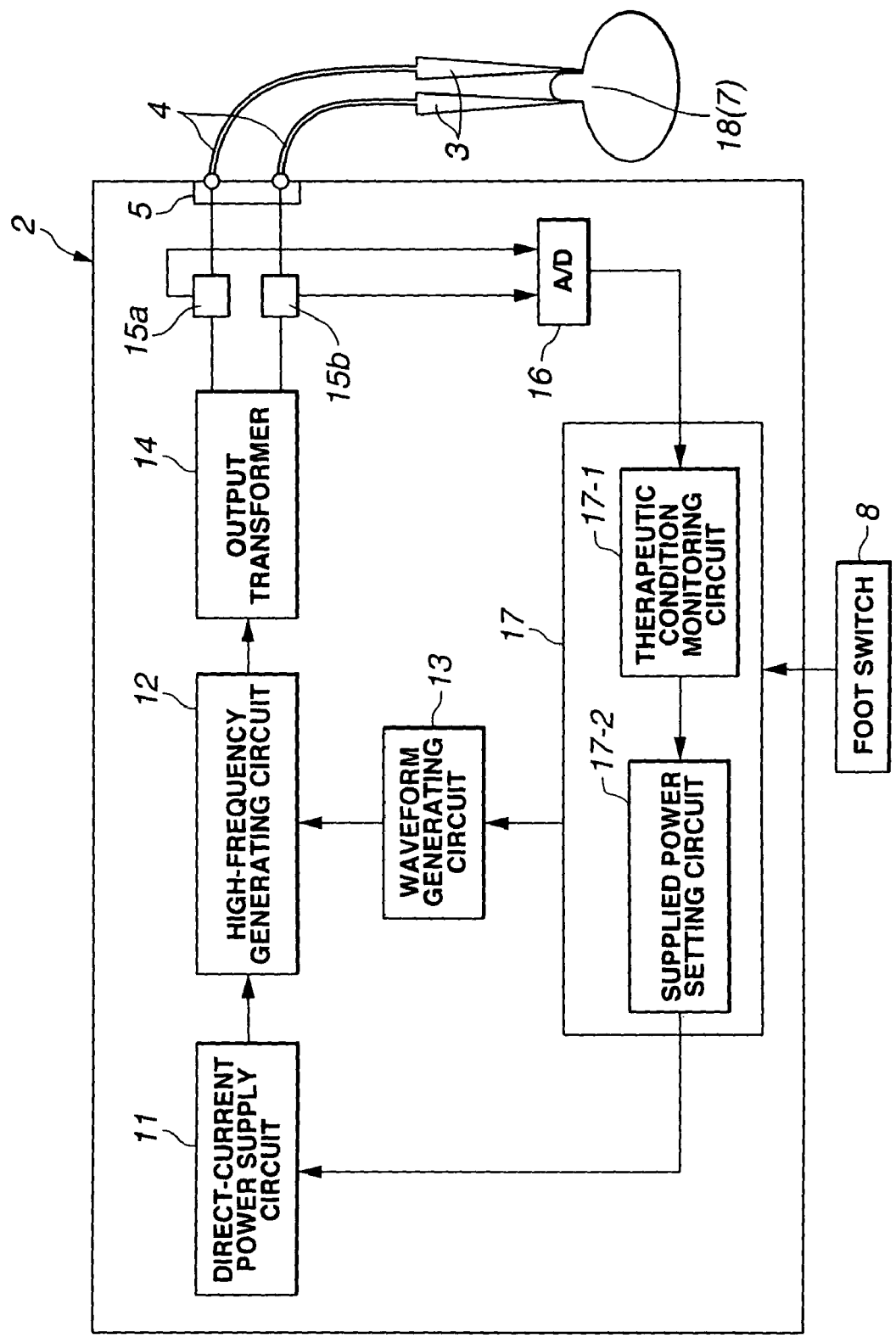
FIG. 2 is a block diagram depicting the structure of a high frequency cauterizing power supply unit.
Figure 3:
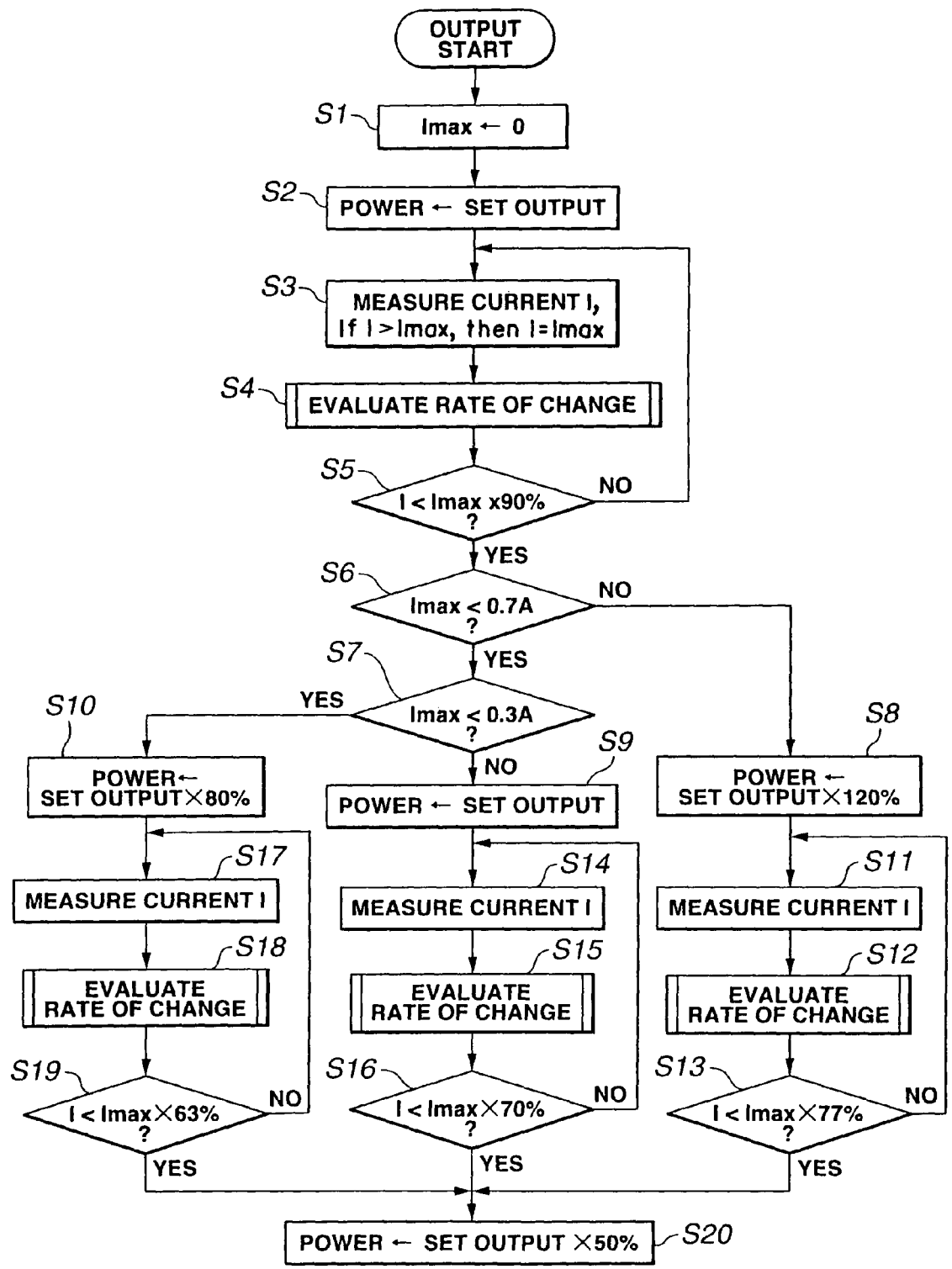
FIG. 3 is a flow chart depicting the controlling steps of the control circuit in FIG. 2.
Figures 4A, 4B:
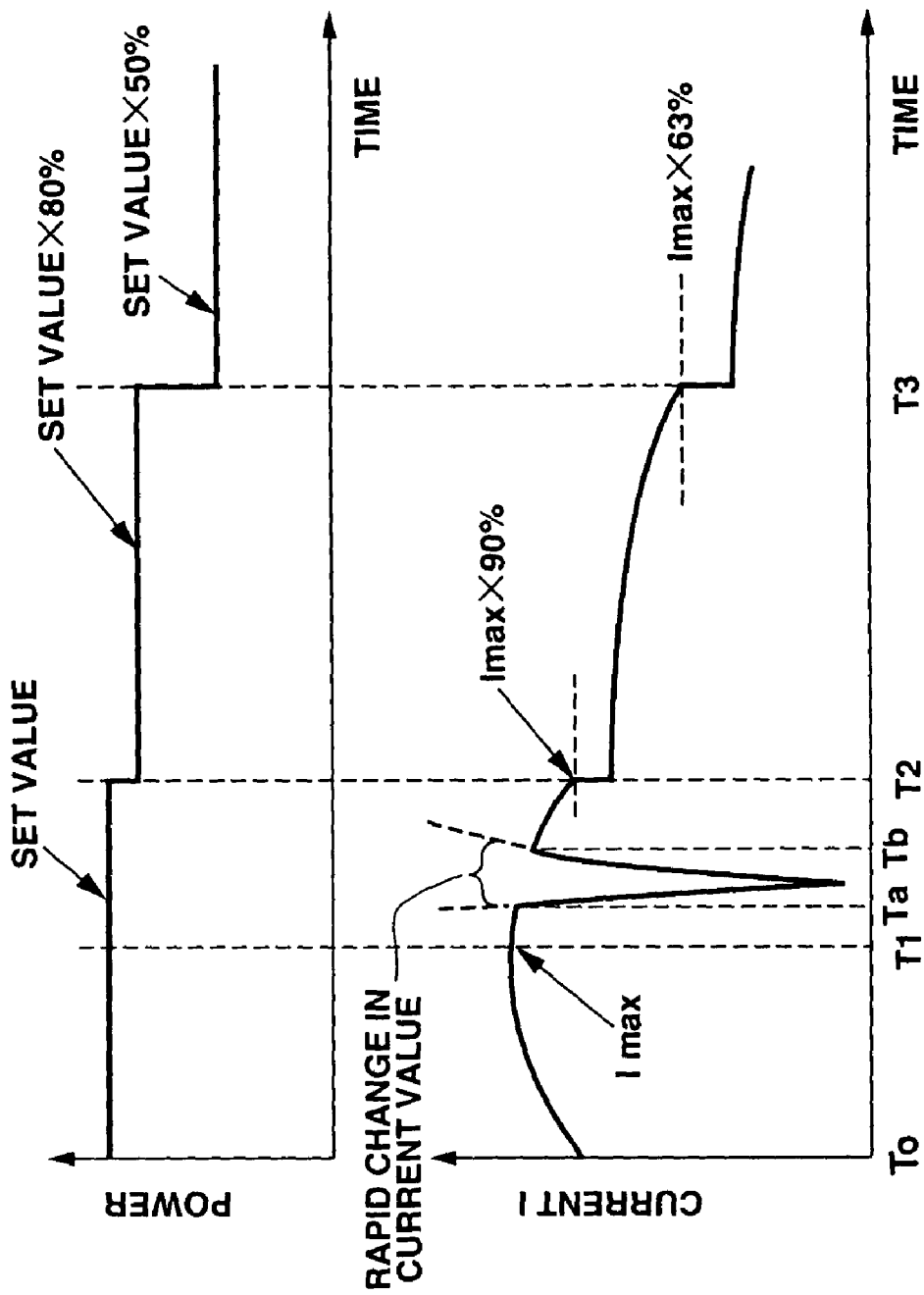
FIG. 4A is a diagram illustrating the manner in which preset power values vary with the temporal variations of a high frequency power supply.
FIG. 4B is a diagram illustrating the manner in which electric current values vary with the temporal variations of a high frequency power supply.
Figure 5:
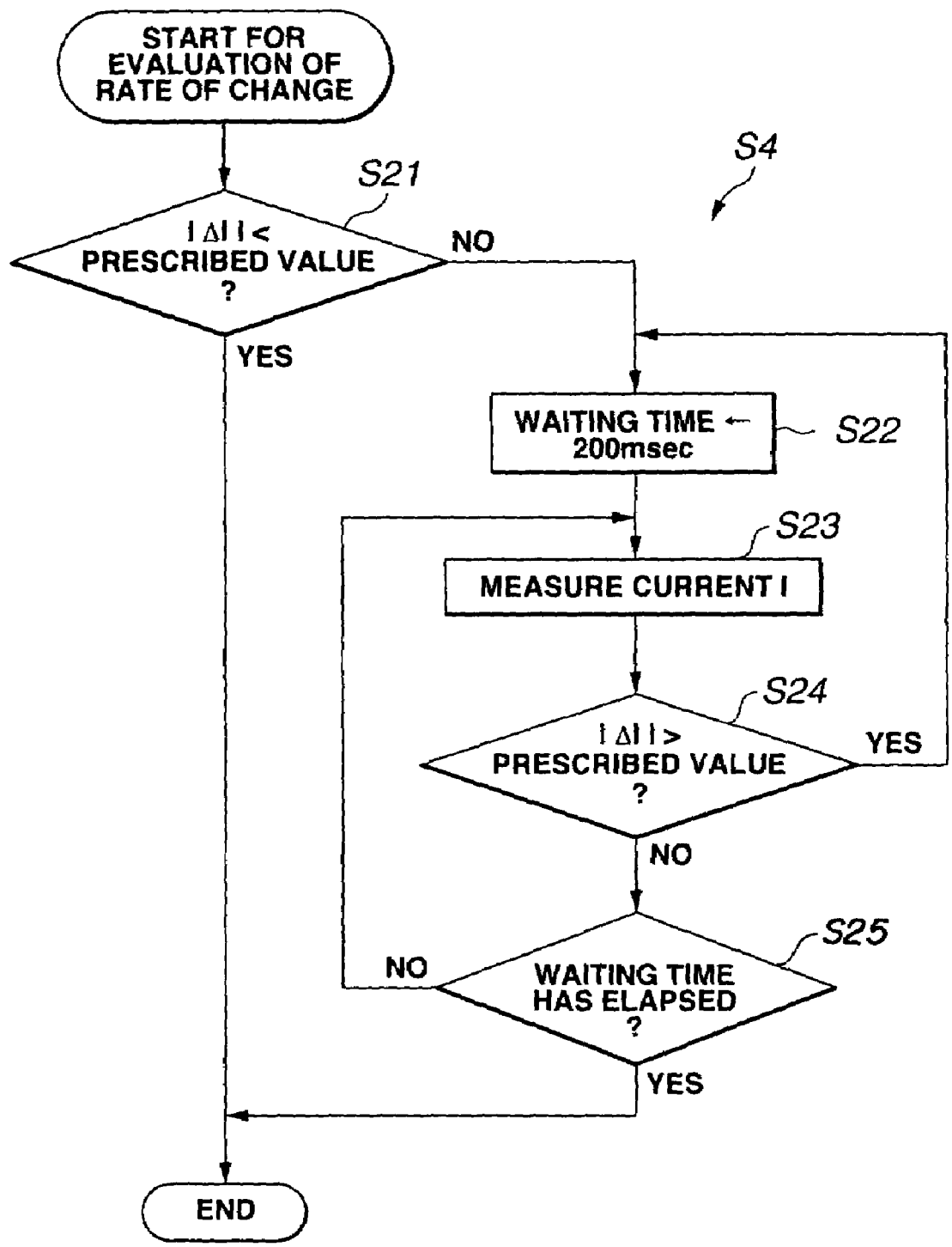
FIG. 5 is a flow chart depicting in detailed form the processing involved in measuring the rate of change of electric current.
Figure 6:
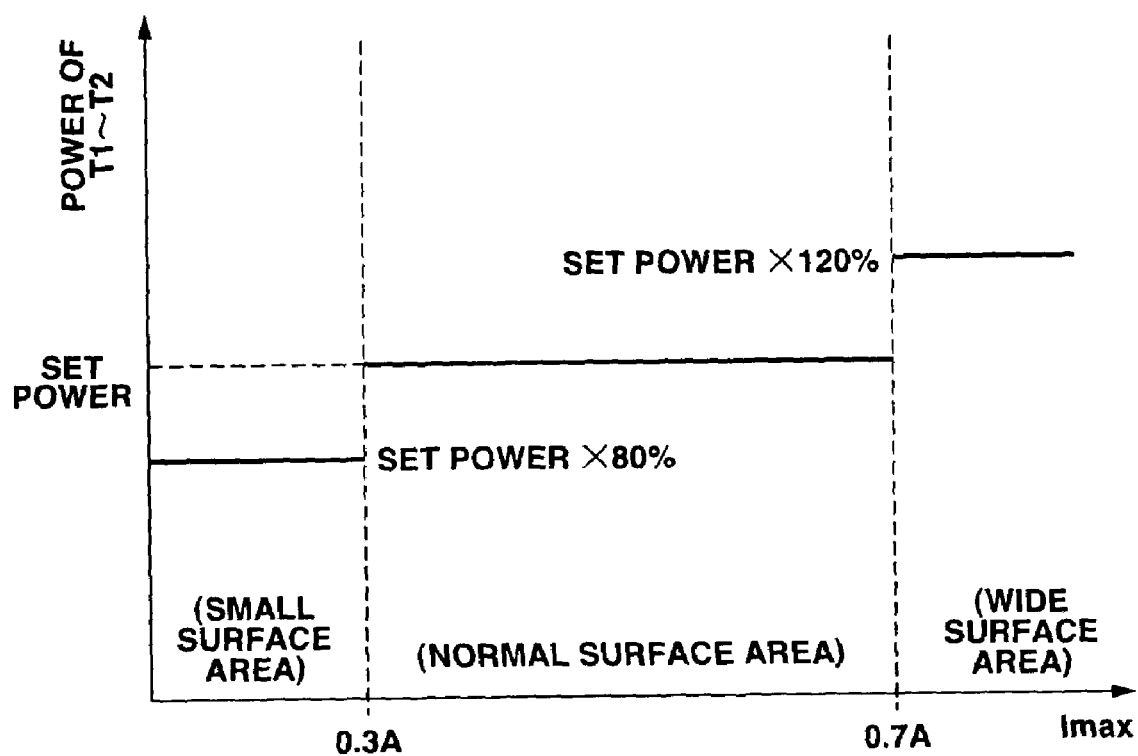
FIG. 6 is a diagram depicting the relation between the maximum value of electric current and the set value of electric power.

FIGS. 1 to 6 pertain to a first embodiment of the present invention. FIG. 1 is a diagram depicting the general layout of a high frequency cauterizing unit pertaining to a first embodiment of the inventive electric operation apparatus. FIG. 2 is a block diagram depicting the structure of a high frequency cauterizing power supply unit. FIG. 3 is a flow chart depicting the controlling steps of the control circuit in FIG. 2. FIGS. 4(A) and 4(B) are diagrams illustrating the manner in which preset power values and electric current values vary with the temporal variations of a high frequency power supply unit. FIG. 5 is a flow chart depicting in detailed form the processing involved in measuring the rate of change of electric current. FIG. 6 is a graph depicting the relation between the maximum value of electric current and the set value of electric power.

As can be seen in FIG. 1, the high frequency cauterizing unit 1 pertaining to the first embodiment of the inventive electric operation apparatus comprises a high frequency cauterizing power supply unit 2 for feeding high frequency cauterizing electric power, wherein the high frequency cauterizing power supply unit 2 is connected by a connector 5 to connector cables 4 whose tips are provided with electrodes 3 (treatment means). High frequency cauterizing electric power for therapeutic purposes is fed via these electrodes 3 to a patient 7 on a bed 6 to perform a therapeutic treatment (surgical treatment).

A foot switch 8 is an example of a device designed for switching on and off the high frequency cauterizing electric power and connected to the high frequency cauterizing power supply unit 2. The electrodes 3 may be single electrodes or multiple electrodes.

As can be seen in FIG. 2, the high frequency cauterizing power supply unit 2 has a direct current power supply circuit 11 connected to a commercial power source (not shown) and designed for converting an alternating current power supply to a direct current power supply and feeding electric power from this direct current power supply, and a high frequency generating circuit 12 energized by the direct current power supply from the direct current power supply circuit 11 and designed to oscillate at a high frequency and to generate high frequency power (high frequency current). The high frequency cauterizing power supply unit 2 further comprises a waveform generating circuit 13 for controlling the waveform of the high frequency current outputted by the high frequency generating circuit 12, an output transformer 14 for outputting the high frequency current from the high frequency generating circuit 12 to the electrodes 3, current sensors 15a and 15b for sensing the output current outputted by the output transformer 14, an A/D converter circuit 16 for the A/D conversion of the electric current value sensed by the current sensors 15a and 15b, and a control circuit 17 for controlling the direct current power supply circuit 11 and the waveform generating circuit 13 on the basis of digitized current data from the A/D converter circuit 16. The power supplied from the direct current power supply circuit 11 is varied and the output of the high frequency generating circuit 12 is controlled based on a setting signal from the control circuit 17. The control circuit 17 has a therapeutic condition monitoring circuit 17-1 and a supplied power setting circuit 17-2.

The connector cables 4 are connected to the connector 5, and the affected tissue 18 or other organ of the patient 7 is cauterized at a high frequency with the aid of the electrodes 3.

One of the two current sensors 15a and 15b (for example, the current sensor 15a) senses the current flowing from one of the electrodes 3 to the patient 7 (biological tissue 18), whereas the other current sensor 15b senses the current recovered by the output transformer 14 from the other electrode 3.

The control circuit 17 can control the waveform generated by the waveform generating circuit 13 in accordance with incision, coagulation, or another treatment mode.

The foot switch 8 is connected to the control circuit 17. When the on-switch of the foot switch 8 is stepped on, the control circuit 17 performs a control routine whereby high frequency current is outputted by the high frequency generating circuit 12. When the off-switch is stepped on, the control circuit 17 stops the output of the high frequency current.

According to the present embodiment, the control circuit 17 is configured such that the current flowing through the biological tissue 18 is constantly monitored when the foot switch 8 is closed and a high frequency current used for therapeutic purposes is allowed to flow in order to perform a high frequency treatment on the biological tissue 18 of the patient 7, as described below. The monitoring is carried out using the therapeutic condition monitoring circuit 17-1 described below. Specifically, when the high frequency current is allowed to flow through the biological tissue, this current is measured at predetermined sampling intervals, and the electric current data obtained by such measurements are monitored and stored in a storage device (not shown). Variations in the therapeutic condition can be sensed (detected) by sensing variations in the high frequency current on the basis of the electric current data thus monitored. Optimal therapeutic treatment independent of the contact area or the like can be performed by performing a control routine in which high frequency power is varied based on the magnitude of these variations.

For this reason, the control circuit 17 comprises a therapeutic condition monitoring circuit 17-1 for sensing variations in the high frequency current on the basis of sampled electric current data obtained over time, and monitoring the therapeutic condition by means of the high frequency current. The control circuit 17 also controls power supply and performs the functions of a supplied power setting circuit 17-2 for outputting a setting signal to a direct current power supply circuit in order to control high frequency power on the basis of the monitoring results.

In more specific terms, the electric current data to be inputted are stored over time by the control circuit 17 to an internal memory or the like (that is, the data are stored over time in a memory or the like as a time sequence) in order to monitor the digitized electric current data from the A/D converter circuit 16 over time, and temporal variations in the electric current data are monitored. The electric current data are monitored from the moment these electric current data reach a maximum value up to the moment the electric current value decreases to a standard value slightly below the maximum value, and variations in tissue degeneration are thus estimated and analyzed. The standard value is set based on past electric current data. The control circuit 17 also monitors the absolute value of the rate of change of the electric current data.

Once the electric current data fall below the standard value, the control circuit 17 determines the condition of the therapeutic treatment on the basis of the maximum value of electric current, that is, determines the magnitude of the contact area between the electrodes 3 and the biological tissue 18 and the progress of tissue degeneration. The supplied power setting circuit 17-2 outputs a setting signal to the direct current power supply circuit 11 in order to set the high frequency power to a power output level suitable for performing a coagulation treatment on the contact area thus determined. The coagulation treatment is continued at the power output thus set. Variations (variations in therapeutic condition with coagulation treatment) are monitored to determine whether the electric current has decreased to the target value (or threshold value) corresponding to coagulation completion. The coagulation treatment is continued at the preset power output if the monitoring results show that the current has not decreased below the target value, and when it is concluded that the coagulation treatment has been completed, the power is adjusted such that the output is reduced by about half, making it possible to perform the coagulation treatment in a consistent manner independently of the surface area.

In other words, the current flowing through the system has a low maximum value when only a small contact area is formed by the biological tissue 18 held or otherwise secured with the electrodes 3, and the maximum value of electric current increases with an increase in contact area. In this embodiment, therefore, the electric current is monitored over time, the size of the contact area involved in the therapeutic treatment is tentatively set in accordance with the maximum value of the electric current thus measured, the high frequency electric current output is modified and set to a prescribed level in accordance with the tentative setting, and the coagulation treatment is continued. Specifically, the high frequency electric current output is varied in accordance with this estimated and fixed value. As a result, performing a coagulation treatment at a set output corresponding to the size of the contact area ultimately allows the coagulation treatment to be performed in a consistent manner irrespective of the contact area even when this contact area varies.

In addition, the coagulation treatment can be performed at a power output whose level can be varied in accordance with the contact area. Variations in electric current are monitored in a state corresponding to this set electric power. Completion of the target coagulation treatment is verified by comparing an electric current measurement with a preset target value selected in accordance with each preset power value. At the time of completion, that is, when completion conditions have been achieved, the coagulation treatment is considered to be completed, and a control routine is performed in order to reduce the preset power value, making it possible to perform the coagulation treatment in a consistent manner irrespective of the size of the contact area.

If the contact area is wide or large, the treatment is performed at a preset power value obtained by increasing the electric power above the level adopted for a small contact area, making it possible to save time and to accelerate the coagulation treatment. If the contact area is small, the power set output is reduced, and the rate of tissue degeneration is brought within a range readily discernible by the specialist, making it easier to identify or otherwise categorize the coagulation state.

The rate of change of the electric current thus registered is measured as an absolute value, and it is determined whether this value is less than a prescribed value in order to prevent coagulation from being mistakenly identified as completed when an unstable contact has been established between the biological tissue 18 and the electrodes 3.

Operation of the embodiment thus configured will now be described with reference to the flow chart shown in FIG. 3.

Stepping on the foot switch 8 causes a control routine to be started in accordance with the process that follows the start of output in FIG. 3.

Specifically, stepping on the foot switch 8 causes the control circuit 17 to set the maximum value Imax of electric current to 0 in step S1. In the subsequent step S2, the control circuit 17 controls the direct current power supply circuit 11 and the waveform generating circuit 13 in a manner such that power output matches a predetermined set output. The corresponding set output is selected in advance in accordance with the treatment mode.

FIGS. 4(A) and 4(B) depict an example in which high frequency power and high frequency current vary over time during a coagulation treatment. At time T0, the high frequency power is outputted according to a preset value.

The subsequent procedures, which extend from the measurement of current I in step S3 to step S5, are repeated at regular sampling intervals until the electric current value I (also referred to as "current I") falls below the maximum value Imax of electric current×90%.

Specifically, measuring current I in step S3 entails sensing the high frequency current by the current sensors 15a and 15b, converting the result to digital format by the A/D converter circuit 16, measuring the digitized value, and transmitting the current I thus measured to the control circuit 17.

Therefore, it is possible for the control circuit 17 to recognize the maximum value among values of the current I received a plurality of times at regular sampling intervals as $I_{max}$.

The control circuit 17 then determines the absolute value |ΔI| of the rate of change of current I (hereinafter abbreviated as "rate of change |ΔI| of current I") in step S4. This step S4 is shown in detail as steps S21 to S25 in FIG. 5.

When the procedure involved in evaluating the rate of change is started, the rate of change |ΔI| of current I is calculated based on the previous current I measurement in step S21 and the current measurement, and a comparison is made to determine whether the calculation result is less than a prescribed value (or threshold value).

If the rate of change |ΔI| is less than the prescribed value (or threshold value), the procedure involved in evaluating the rate of change is terminated, and the operation proceeds to step S5 in FIG. 3. Conversely, if |ΔI| is not less than the prescribed value (threshold value), the procedures involved in steps S22 to S25 are repeated until the rate of change |ΔI| falls below the prescribed value (or threshold value), and the operation does not proceed to step S5.

Specifically, the waiting time is set to 200 msec in step S22 when the rate of change |ΔI| exceeds the prescribed value (or threshold value). In the subsequent step S23, current I is measured, and a comparison is then performed in the subsequent step S24 to determine whether the rate of change |ΔI| is greater than the prescribed value (or threshold value). The operation proceeds to the next step S25 if this is not the case, that is, if the rate of change |ΔI| is less than the prescribed value, and returns to step S22 if this condition is met (rate of change |ΔI| is greater than the prescribed value).

The passage of the waiting time is further awaited in step S25 if the rate of change |ΔI| is less than the prescribed value (or threshold value) in this manner. After the rate of change |ΔI| has thus been reduced to a level below the prescribed value (or threshold value) and stabilized, the process involved in evaluating the rate of change is completed and the operation proceeds to step S5 in FIG. 3.

In step S5, a comparison is made between current I and the maximum value Imax of electric current×90%, that is, the change in the electric current is sensed. The operation proceeds to the subsequent step S6 if current I is less than the maximum value Imax of electric current×90%. Conversely, the operation returns to step S3 and the same processing is repeated if it is greater than the maximum value Imax of electric current×90%.

In the example shown in FIG. 4(B), current I reaches the maximum value of Imax of electric current×90% at time T2 and then decreases. Because current I is less than maximum value Imax×90% at time T2, the operation proceeds to a step for determining whether current $I_{max}$ (maximum value Imax of electric current) is less than 0.7 A in step S6 at time T2.

In this example, the rate of change |ΔI| during period Ta to Tb (part of period T1 to T2) is kept greater than the prescribed value (or threshold value).

Current I is thus less than the maximum value Imax of electric current×90% during period Ta to Tb, so the procedures performed in step S4 prior to evaluating whether the current I in step S5 is less than the maximum value Imax of electric current×90% (that is, the procedures performed in steps S21 to S25 in FIG. 5) do not include the evaluation performed in step S5.

It is determined in steps S6 to S7 in FIG. 3 whether the maximum value Imax of electric current is less than 0.7 A (ampere) and the maximum value Imax is less than 0.3 A (ampere), and electric power is modified in accordance with results that correspond to these conditions. The amperages (0.7 and 0.3) cited here are merely examples of threshold values, which are determined according to the standard size of the surface area to be treated.

Specifically, a comparison is made in step S6 to determine whether the maximum value Imax is less than 0.7 A. If the value is equal to or greater than 0.7 A, it is concluded in step S8 that a large contact area has been established, and the power output is raised to 120% of the preset power value. If the maximum value Imax is less than 0.7 A but greater than 0.3 A, it is concluded that the contact area has regular dimensions (as shown in step S9) and the power output is brought to a set output value.

If the maximum value Imax is less than 0.3 A, it is concluded that the contact area is small (as shown in step S10), and the electric power is brought down to 80% of the preset output.

FIG. 6 shows the relation between the maximum value Imax of electric current and the preset value of electric power. The size of the contact area that constitutes therapeutic condition is evaluated in accordance with the maximum value Imax of electric current sensed during a measurement in the manner described above, and the preset power is set in accordance with the contact area thus evaluated.

In the example shown in FIGS. 4(A) and 4(B), Imax is less than 0.3 A, so the electric power is brought down to 80% of the setting. The preset power value is thus varied in steps S8 to S10 in accordance with the maximum value Imax of electric current.

Current I is then measured, for example, in the step S11 (in the same manner as in step S3) subsequent to step S8, and the rate of change |ΔI| is evaluated in the subsequent step S12 (in the same manner as in step S4). In the subsequent step S13, coagulation completion is confirmed by determining whether current I is less than the threshold value of the previously calculated and set target value (maximum value Imax of electric current×77%). If current I is greater than the target value, that is, the threshold value, the operation returns to step S11, the high frequency current is kept flowing, and a coagulation treatment is performed. If current I is less than the threshold value, that is, the target value (maximum value Imax of electric current×77%), it is concluded that the coagulation treatment has been completed, and the electric power in step S20 is brought down to 50% of the set output.

In steps S14 to S16, which follow step S9, current I is measured in the same manner as in step S3, and the rate of change |ΔI| is determined in the same manner as in step S4. Coagulation completion is verified by determining whether current I is less than a threshold value that is 70% of Imax. If the value of current I is equal to or greater than the threshold value, the operation returns to step S14, the high frequency current is kept flowing, and a coagulation treatment is performed. Conversely, the coagulation treatment is assumed to be completed if the condition of step 16 are satisfied, so the operation proceeds to step S20 and the electrical power is brought down to 50% of the set output value.

In steps S17 to S19, which follow step S10, current I is measured in the same manner as in step S3, and the rate of change |ΔI| is determined in the same manner as in step S4. Coagulation completion is verified by determining whether current I is less than a threshold value that is 63% of Imax. If the value of current I is equal to or greater than the threshold value, the operation returns to step S17, the high frequency current is kept flowing, and a coagulation treatment is performed. Conversely, the coagulation treatment is assumed to be completed if the condition of step 19 are satisfied, so the operation proceeds to step S25 and the electrical power is brought down to 50% of the set output value.

The steps from step S6 to step S20 correspond to period T2 to T3 in FIGS. 4(A) and 4(B). Because current I drops below 63% of the maximum value Imax of electric current at time T3, the control circuit 17 concludes that the coagulation treatment has ended and reduces the preset power value to 50% of the preset value.

The present embodiment has the following merits.

The present embodiment entails defining variations in the output of a high frequency current on the basis of values measured by the control circuit 17, making it possible to verify coagulation completion in a consistent manner and to prevent tissue from coagulating or adhering to electrodes irrespective of the contact area between the tissue and the electrodes 3.

In conventional practice, coagulation takes time when a very large contact area is established between the electrodes 3 and the tissue, but the present embodiment allows the coagulation time to be reduced because electric power is increased when the electric current has a substantial maximum value. In addition, the tissue degeneration rate can be brought within a range readily discernible by the specialist and the coagulation treatment can be facilitated because the electric power is reduced in accordance with the size of a small surface area.

Although the value of electric current is used in the present embodiment, the same merits can be obtained using other measured values or parameters. For example, the electric power can be increased at low impedance by performing the same control routine the basis of impedance variations. Voltage, impedance, electric power, phase difference, or the like may be used.

An unstable contact between the electrodes 3 and the tissue affects tissue impedance and causes it to vary. In conventional practice, this results in coagulation being incorrectly termed as completed. In the present embodiment, variations in current I are monitored, making is possible to accurately verify coagulation completion even in the case of an unstable contact the electrodes 3 and the tissue.

A second embodiment will now be described.

Figure 7:
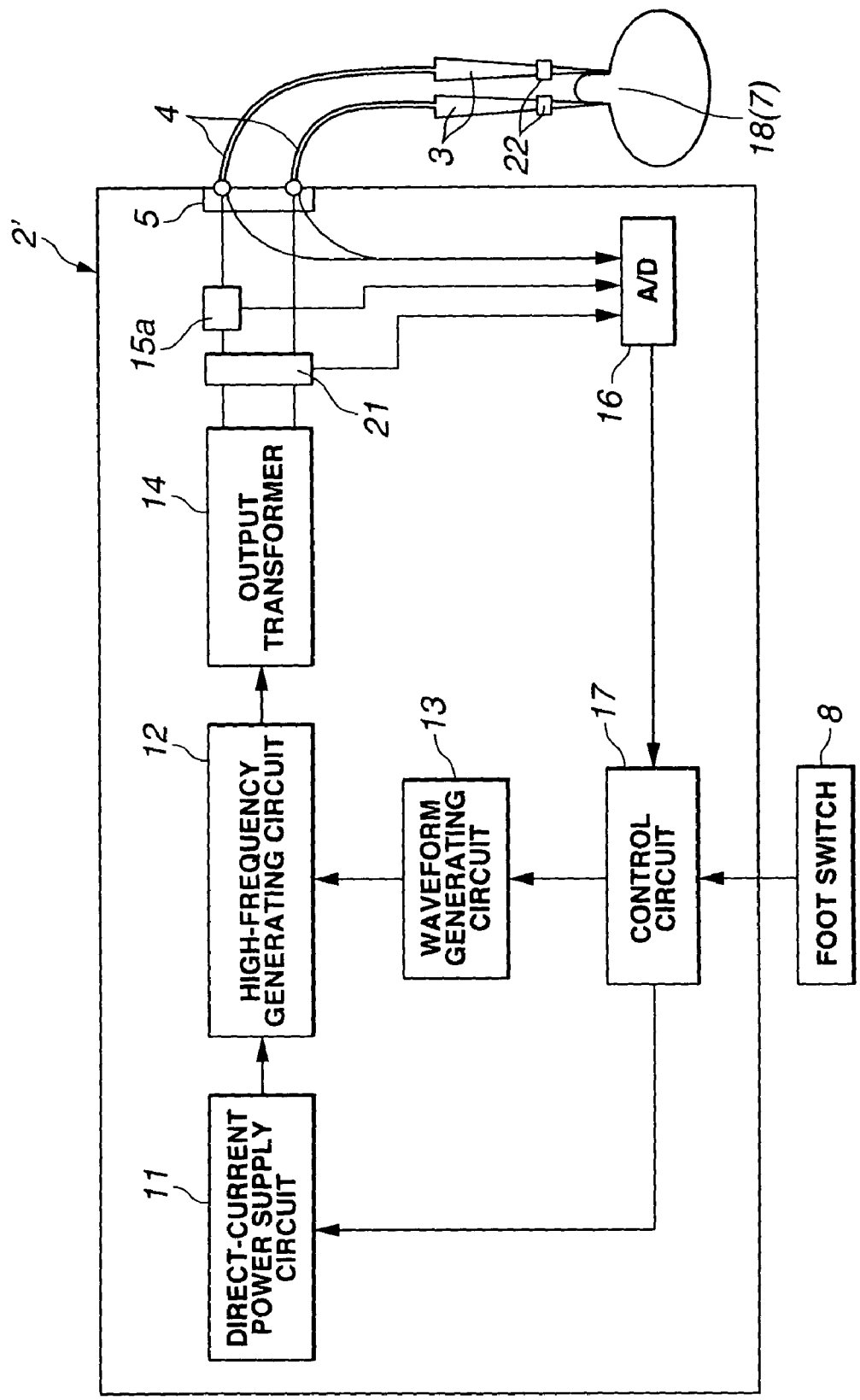
FIG. 7 is a block diagram depicting the structure of a high frequency cauterizing power supply unit pertaining to a second embodiment of the present invention.
Figure 8:
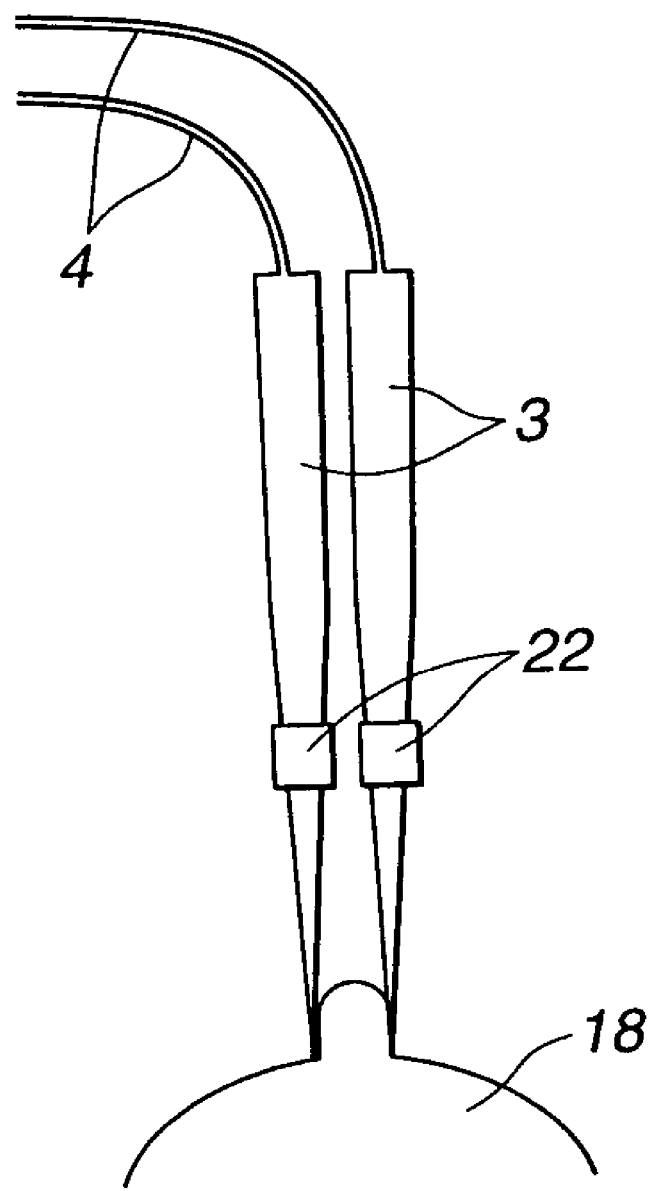
FIG. 8 is an expanded view of an electrode.
Figure 9:
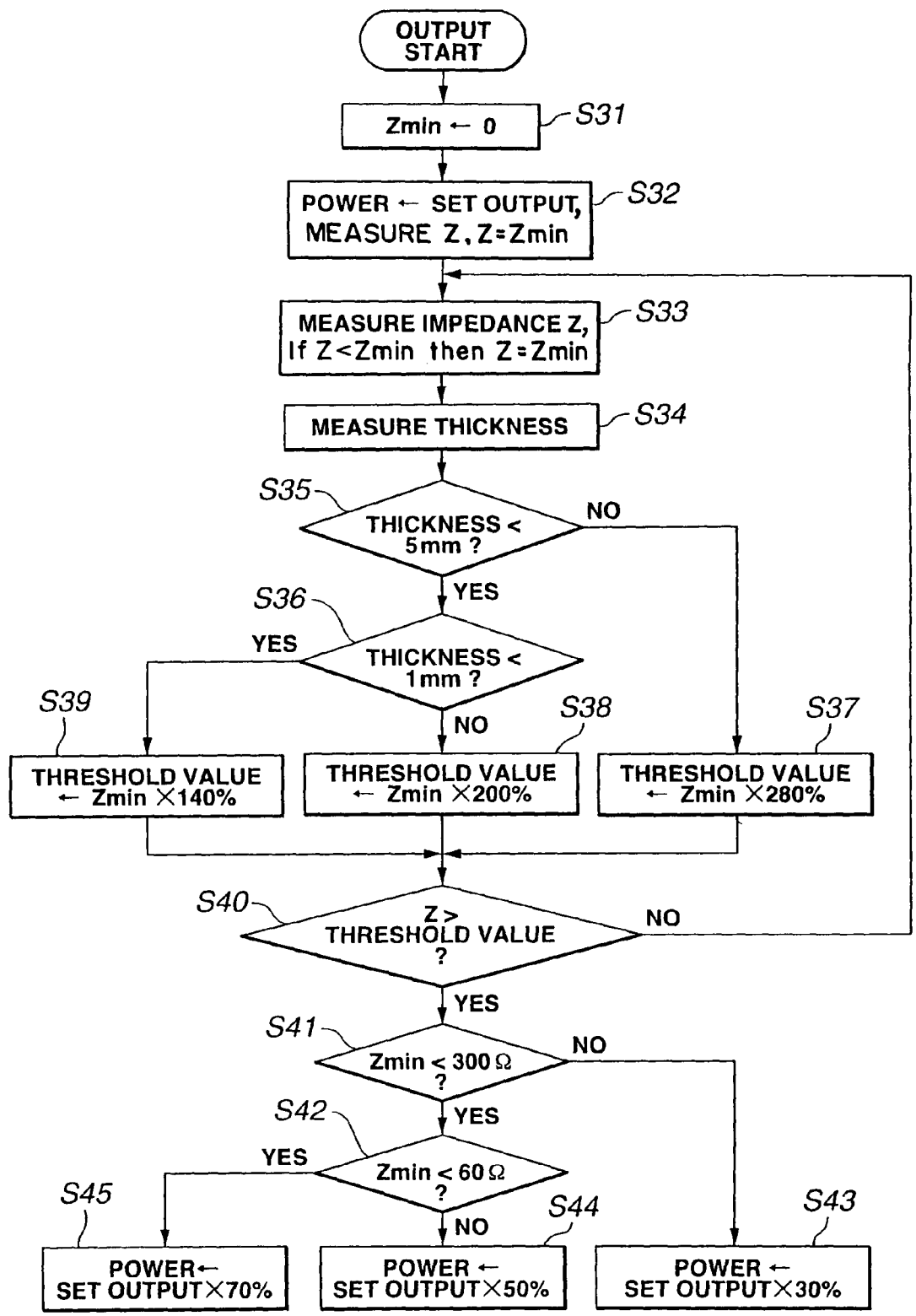
FIG. 9 is a flow chart depicting the control steps of a control circuit.
Figure 10:
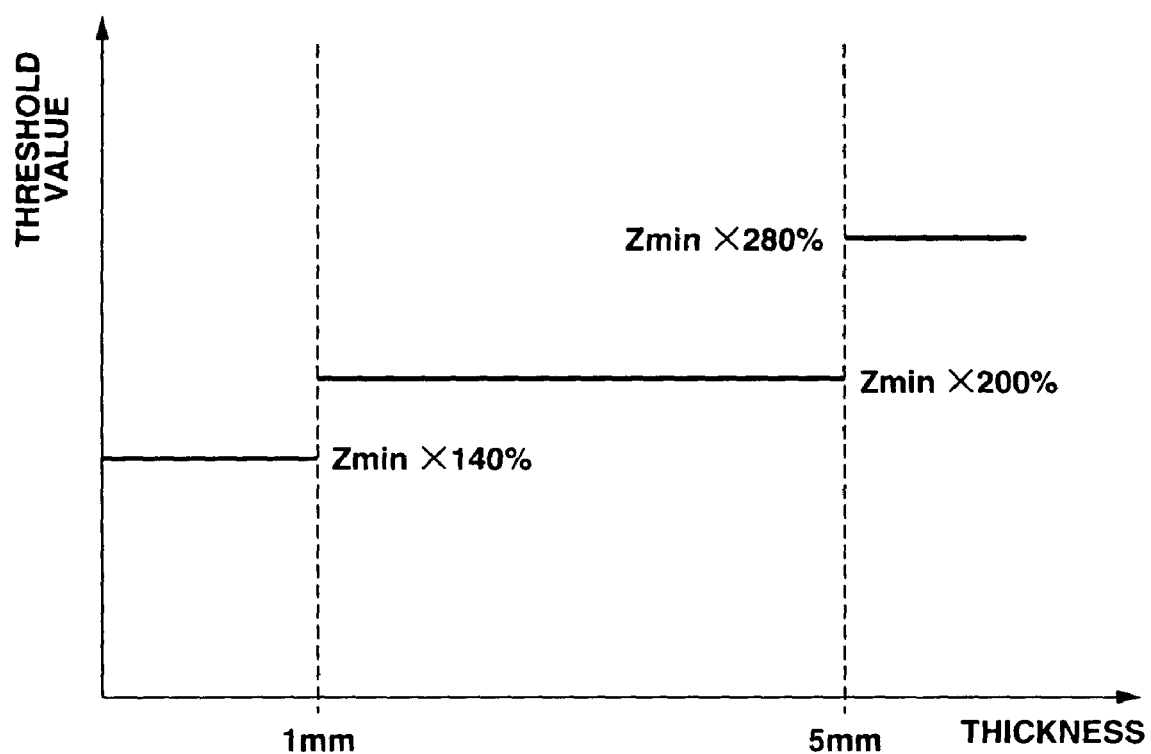
FIG. 10 is a diagram illustrating the threshold value established in accordance with thickness.

The second embodiment of the present invention will now be described with reference to FIGS. 7 to 12. FIG. 7 is a block diagram depicting the structure of a high frequency cauterizing power supply unit. FIG. 8 is an expanded view of an electrode. FIG. 9 is a flow chart depicting the control steps performed by the control circuit in FIG. 7. FIG. 10 is a diagram illustrating the threshold value established in accordance with thickness. FIG. 11 is a diagram illustrating a specific example of the manner in which the set value of electric power and the impedance vary with time when a high frequency current is allowed to flow. FIG. 12 is a diagram illustrating the manner in which the value of electric power is set in accordance with the minimum impedance value.

The second embodiment is substantially similar in structure to the first embodiment. Consequently, the differences alone will be described, identical components will be designated using the same symbols, and their description will be omitted.

The high frequency cauterizing power supply unit 2' pertaining to this embodiment is configured such that the two terminals of an output transformer 14 are provided with a voltage sensor 21 for sensing the voltage between the two terminals, as shown in FIG. 7. The signal from the voltage sensor 21 is inputted together with the signal from a current sensor 15a to a control circuit 17 via an A/D converter circuit 16, and voltage and current are measured. The control circuit 17 determines impedance by dividing the voltage value by the current value, and monitors the result. The control circuit 17 has the same structure as the control circuit 17 in FIG. 2 and comprises a therapeutic condition monitoring circuit 17-1 and a supplied power setting circuit 17-2. These circuits are omitted from FIG. 7.

Specifically, whereas electric current is monitored in the first embodiment, it is impedance that is monitored in the present embodiment.

In addition, the electrodes 3 pertaining to the present embodiment are configured such that the two electrodes 3 are provided with distance sensors 22 for measuring the distance between the electrodes 3, as shown in FIG. 8. The signal from the distance sensors 22 is inputted as distance information (thickness information related to the portion of the biological tissue 18 being treated) from the connector 5 in FIG. 7 to the A/D converter circuit 16 in the high frequency cauterizing power supply unit 2' via the signal lines in the connector cables 4. The distance, or thickness, information undergoes an A/D conversion and is presented to the control circuit 17.

Hall sensors (sensors featuring Hall elements) that utilize magnetism, optical sensors that utilize reflected light, sensors having mechanical contacts, or any other sensors can be used as the distance sensors 22. When, for example, magnetism is used, one of the two distance sensors 22 produces magnetism of prescribed intensity, a sensed output corresponding to this magnetic intensity is obtained by the other Hall sensor, and distance is thereby sensed.

Operation of the embodiment thus configured will now be described. The control circuit performs a control routine according to the flow chart shown in FIG. 9.

Steps S31 to S33 are substantially the same as in the first embodiment. In the present embodiment, however, impedance Z is calculated by dividing a voltage value by a current value, and this impedance is used to perform the control routine.

Specifically, 0 is substituted for the minimum value (minimum impedance value) Zmin of impedance Z in step S31, (high frequency) electric power is set to a predetermined set output level in the subsequent step S32, and impedance Z is measured in step S33.

In the subsequent step 534, the thickness (distance) of the tissue sandwiched between the electrodes 3 and treated using these electrodes 3 is determined by calculation on the basis of the thickness information provided by the distance sensors 22. In the subsequent steps S35 to S39, the threshold value of power-reducing impedance Z is determined in accordance with the tissue thickness.

Specifically, it is determined in step S35 whether the thickness is less than 5 mm (millimeters), and if it is indeed less than 5 mm, a comparison is made in step S36 to determine whether the thickness is less than 1 mm. If it is concluded in step S35 that the thickness is no less than 5 mm (is equal to or greater than 5 mm), the threshold value is set to the minimum value Zmin of impedance Z×280% in step S37. If it is concluded in step S36 that the thickness is no less than 1 mm (is equal to or greater than 1 mm but less than 5 mm), the threshold value is set to the minimum value Zmin of impedance Z×200% in step S38. If it is concluded in step S36 that the thickness is less than 1 mm, the threshold value is set to the minimum value Zmin of impedance Z×140% in step S39.

FIG. 10 shows the relation between the threshold value and the thickness thus set. Here, the threshold value is modified according to the measured thickness.

FIGS. 11(A) and 11(B) depict examples in which high frequency power and impedance Z vary over time. Two cases are considered here: a small contact area and a normal contact area between the tissue and the electrodes. In either case the threshold value is Zmin×200% because the thickness is between 1 and 5 mm.

After a thickness-matching threshold value has been set in steps S37 to 39 above, a comparison is made in the subsequent step S40 to determine whether impedance Z exceeds the aforementioned threshold value.

In the case of a negative outcome, the operation returns to step S33, and the procedures performed in steps S33 to S39 are repeated. Conversely, the operation proceeds to the subsequent step S41 if impedance Z exceeds the aforementioned threshold value.

In other words, impedance values are repeatedly calculated at regular sampling intervals, and it is possible for the control circuit 17 to recognize $Z_{min}$ among the impedance values calculated a plurality of times at regular sampling intervals.

In steps S41 to 45, the electric power is brought down to the value determined based on the minimum value Zmin of impedance Z.

Specifically, it is determined in step S41 whether the minimum value Zmin of impedance Z is less than 300 Ω. Because the contact area cannot be small when this value is less than 300 Ω, a comparison is made in step S42 to determine whether the minimum value Zmin of impedance Z is less than 60 Ω.

In this case, the electric power is brought down to the level of set output×30% in step S43 if the minimum value Zmin of impedance Z in step S41 is no less than 300 Ω (is 300 Ω or greater), that is, if the contact area is small. The contact area is considered to be normal, or standard if the minimum value Zmin of impedance Z is less than 300 Ω and the minimum value Zmin of impedance Z is found to be no less than 60 Ω (that is, 60 Ω or greater but less than 300 Ω) in step S42, so the electric power is set at the level of preset output×50% in step S44. In addition, the contact area is considered to be substantial if the minimum value Zmin of impedance Z is found to be less than 60 Ω in step S42, so the electric power is brought to the level of preset output×80% in step S45.

FIG. 12 depicts the relation between electric power and the minimum value Zmin of impedance Z thus set. The size of the contact area is evaluated on the basis of impedance, and the electrical power value is modified according to the evaluation results.

In the aforementioned FIGS. 11(A) and 11(B), the minimum value Zmin of impedance Z is 300 Ω or greater when the surface area is small, and the minimum value Zmin of impedance Z is between 60 Ω and 300 Ω when a standard contact area is established, so the electric power is reduced to the level of set output×30% and set output×50%, respectively.

The present embodiment has the following merits.

In addition to having all the merits of the first embodiment, the present embodiment entails performing a procedure in which variations in the output of high frequency current are evaluated based on measurement values obtained from the control circuit 17, making it possible to maintain substantially constant tissue degeneration rates irrespective of the contact area between the electrodes 3 and the tissue.

Variations in tissue impedance decrease when the tissue is extremely thick. Whereas a conventional evaluation can yield unsatisfactory results because of tissue carbonization or adherence to the electrodes, the present embodiment is based on thickness measurements and allows coagulation completion to be verified in a consistent manner without being affected by tissue thickness.

Although the present embodiment involves using impedance-containing combinations, the same merits can be obtained using electric current measurements or other measured values or parameters.

A third embodiment will now be described using FIGS. 1, 2, 13, 14, and 15.

Figure 13:
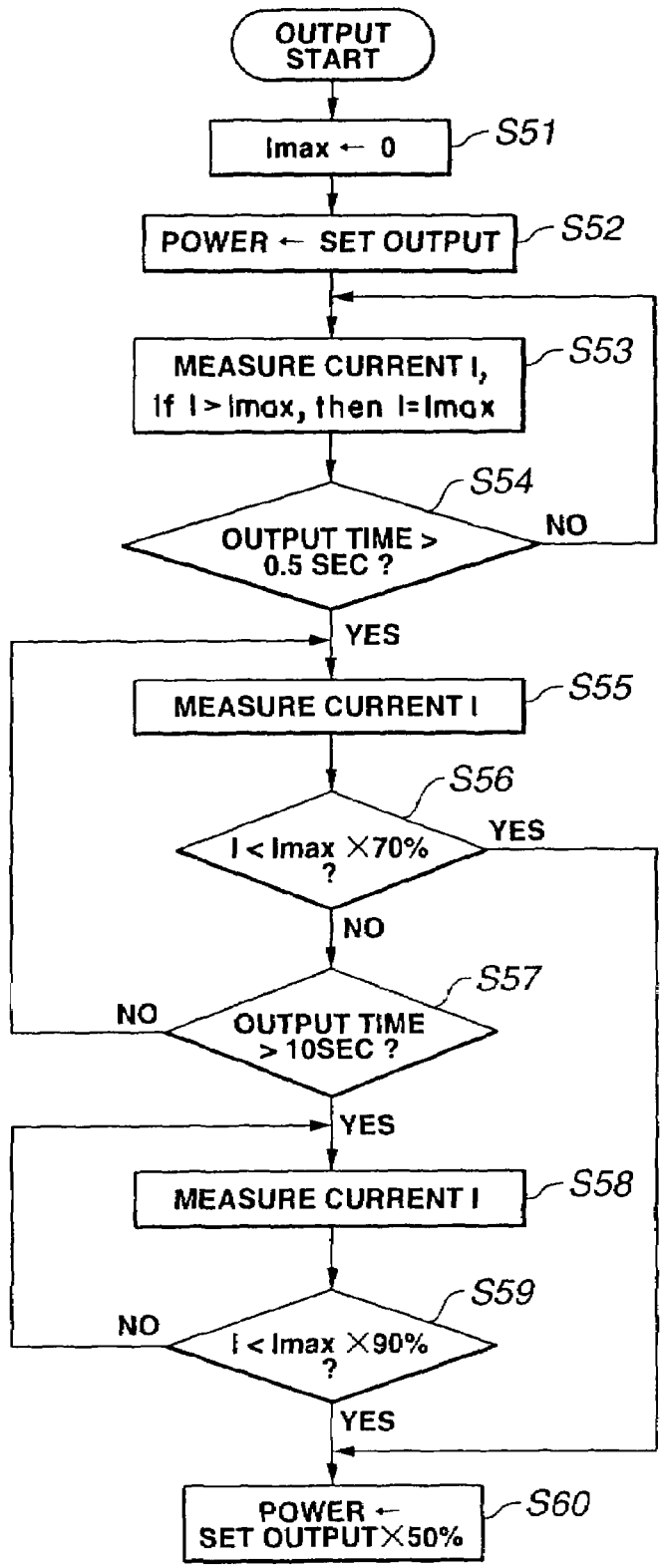
FIG. 13 is a flow chart depicting the control steps performed by a control circuit in accordance with a third embodiment of the present invention.
Figure 14:
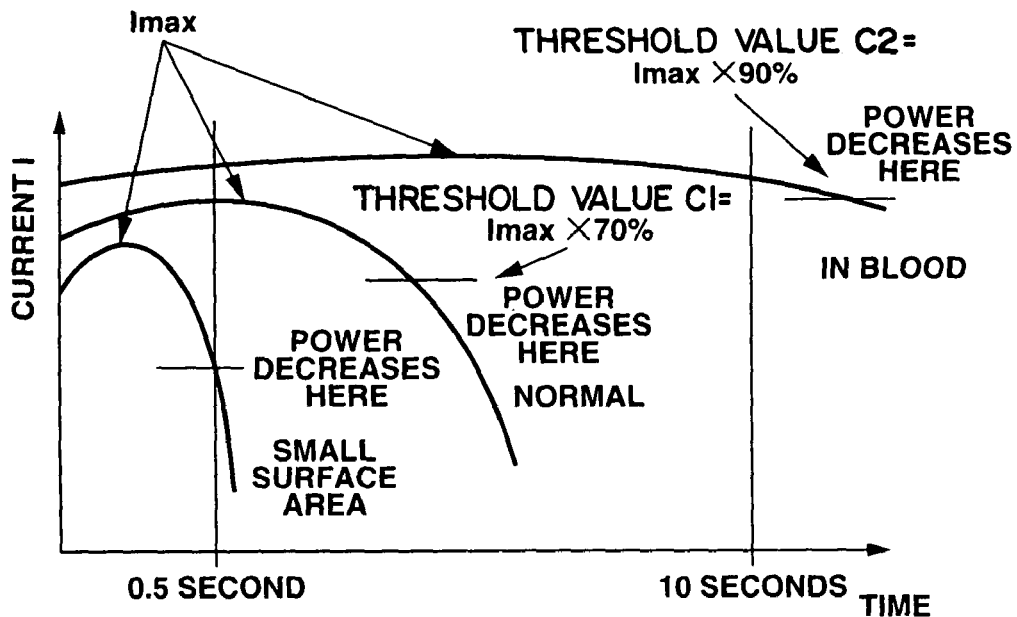
FIG. 14 is a diagram illustrating a process in which the high frequency current of the high frequency cauterizing power supply unit is monitored over time to achieve power control.
Figure 15:
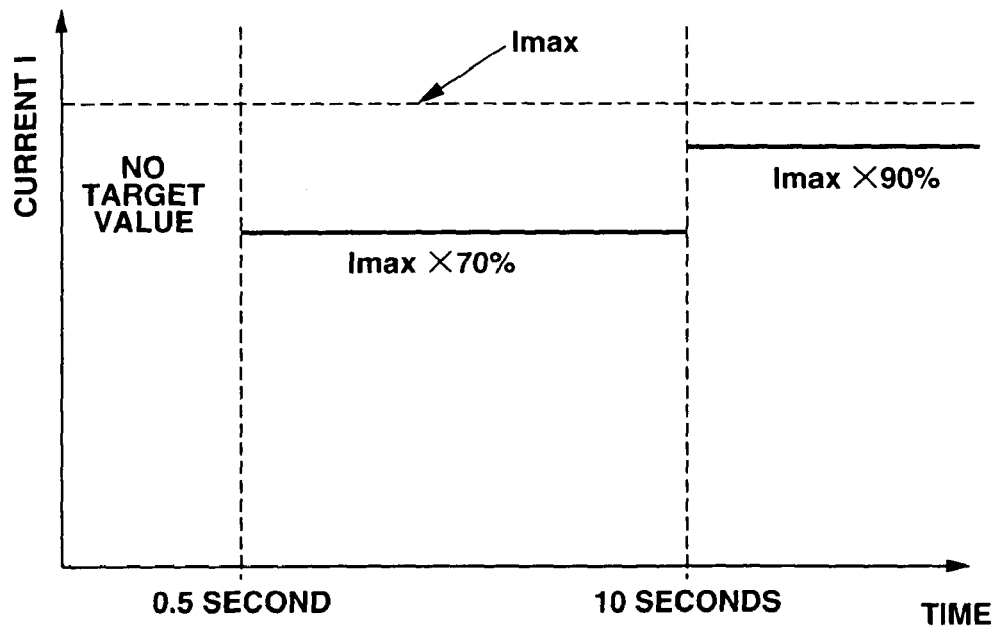
FIG. 15 is a diagram illustrating a process in which the high frequency current of the high frequency cauterizing power supply unit is monitored over time to achieve electric current control.

FIG. 13 is a flow chart depicting the control flow of the control circuit in FIG. 2. FIG. 14 is a functional diagram illustrating a power control routine for monitoring the amount of time corresponding to variations in the electric current value of the high frequency current produced by the high frequency cauterizing power supply unit. FIG. 15 is a functional diagram illustrating an electric current control routine for monitoring the amount of time corresponding to variations in the electric current value of the high frequency current produced by the high frequency cauterizing power supply unit.

Overlapping portions will be omitted from the description because a description has already been given with reference to FIGS. 1 and 2. Here, the control circuit 17 monitors the digitized electric current data from the A/D converter circuit 16 over time (that is, monitors the amount of time corresponding to variations in the electric current value) and senses the therapeutic condition. Specifically, the therapeutic condition is evaluated based on the time needed to achieve the maximum value of sampled electric current.

For example, the electric current data are stored over time in an internal memory or the like, maximum values of the electric current data are monitored based on variations in the electric current data over time, the high frequency output is monitored based on the manner in which the values decrease (drop) after reaching their maximum levels, and therapeutic processes, developments, and the like are monitored based on the monitoring processes or the like. After the electric current data have reached a maximum value, the current electric current data are monitored to determine whether these data have decreased below a preset proportion (target value of treatment termination). The target value is established as a function that is set in advance on the basis of previously sensed therapeutic condition data. It is also determined whether a level below this value has been reached, and the power supplied from the direct current power supply circuit 11 to the high frequency generating circuit 12 is reduced or another control routine performed based on the results of this determination.

According to the present embodiment, the control circuit 17 is first actuated to allow high frequency current to flow when the foot switch 8 is closed to perform, for example, coagulation treatment by passing a high frequency current through the affected tissue 18 of a patient 7, as described below. This case entails monitoring the amount of time corresponding to variations in the electric current value of the high frequency electric power output flowing through the affected tissue 18, the high frequency output is monitored, and the therapeutic condition is sensed (that is, evaluated) based on the operating state of the high frequency current generating means. Once the output has reached the target value corresponding to the end of treatment, the control circuit 17 performs a control routine aimed at reducing the power output. Optimal coagulation treatment can thus be performed irrespective of the surface area or other attributes of the biological tissue 18 held between the electrodes. Consequently, the therapeutic condition monitoring circuit of the control circuit 17 monitors the amount of time corresponding to variations in the electric current value and senses or evaluates the therapeutic condition, and the supplied power setting circuit controls the direct current power supply circuit 11 on the basis of this therapeutic condition and performs a control routine for adjusting the high frequency power.

For example, the current flow tends to rapidly reach its maximum value and to drop off thereafter if the biological tissue 18 held between the electrodes 3 has a small surface area, that is, if the electrodes 3 and the tissue form a small contact area. By contrast, increasing the surface area tends to slowly increase the current flow to its maximum value and to gradually reduce the flow thereafter. Consequently, the therapeutic condition can be evaluated based on the time needed for the electric current to reach its maximum value. According to the present embodiment, which was created with consideration for this fact, the current flow is monitored over time (that is, the electric current is measured at prescribed sampling intervals), and the maximum value is determined based on these data. It is then determined whether the electric current has dropped below a threshold value C1 (which corresponds to a prescribed proportion, for example, 70% of the maximum value) a short time T1 after the start of the current flow. If the current is equal to or less than the threshold value C1, the electric power is set such that reduced power is established immediately after the confirmation of completed coagulation. If the current is greater than the threshold value C1, monitoring is continued, and it is determined whether the current is below the threshold value C1 at time T2, which is greater than time T1. If the current is equal to or less than the threshold value C1, it is concluded that coagulation has ended, and the electric power output is set such that reduced power is established immediately thereafter. The time during which high frequency current is allowed to flow at a given power setting is thus adjusted in accordance with the varying surface area of interposed tissue. Treatments can therefore be performed irrespective of the variations in the surface area of the interposed tissue.

Another feature of the present embodiment is that, after the aforementioned time T2 has elapsed, it is determined whether the value of electric current has fallen below a threshold value C2 (where C1<C2). This value constitutes a prescribed proportion of the maximum value and corresponds to an optimum blood coagulation treatment, as described below. The output value of electric power is reduced in a controlled manner if the result is below the threshold value C2 and coagulation is confirmed to be completed.

In other words, the control circuit 17 for monitoring high frequency current monitors the electric current sampled and measured over time, concludes that a state corresponding to a completed coagulation treatment has been achieved when the electric current being monitored satisfies a given set of conditions, reduces the high frequency current, and terminates the coagulation. Coagulation treatment can therefore be consistently performed irrespective of the contact area without initiating carbonization or the like.

Operation of the embodiment thus configured will now be described with reference to the flow chart in FIG. 13.

Stepping on the foot switch 8 causes the control circuit 17 to set the maximum value Imax of electric current to 0 in step S51. In the subsequent step S52, the control circuit 17 controls the direct current power supply circuit 11 and the waveform generating circuit 13 in a manner such that the power output matches a predetermined value, set output value. The electric current value I (also referred to as "current I") is measured in the subsequent step S53, and the output time is awaited until 0.5 second has elapsed in the subsequent step S54. The 0.5-second interval referred to herein is merely an example, and various other periods can be adopted depending on the power supply setting or the like.

Like the first embodiment, it is possible to recognize $I_{max}$ among values of the current I measured repeatedly at regular sampling intervals.

Steps S55 to S57 are repeated once the 0.5-second period has elapsed. Specifically, the electric current value I is measured in step S55, and it is determined in the subsequent step S56 whether the result is less than 70% of the maximum value Imax of electric current. If the electric current value I is less than the 70% of the maximum value Imax of electric current, it is concluded that coagulation has ended, the operation proceeds to step S60, and the electric power is reduced to 50% of the set output.

If, however, the result in step S56 is equal to or greater than 70% of the maximum value Imax of electric current, it is determined in the subsequent step S57 whether the output time is greater than 10 seconds. If the time is within 10 seconds, the operation returns to step S55, and the processing is repeated. If the electric current value I is still no less than 70% of the maximum value Imax of electric current after 10 seconds have elapsed, the operation proceeds to measuring the electric current value I in step S55.

FIG. 14 depicts an example in which high frequency power and high frequency current vary during a coagulation treatment. In the case shown in the drawing (a case of small contact area), the electric current value I decreases to less than 70% of the maximum value Imax of electric current within 0.5 second of the start of output. It is therefore concluded that coagulation is completed when 0.5 second has elapsed following the start of output, and the set output is immediately reduced to 50% of the preset value.

The normal, standard contact area is greater than a small contact area, in which case the result commonly tends to fall below the threshold value, equal to 70% of the maximum value Imax of electric current, within 0.5 to 10 seconds, so the process is monitored in order to determine whether the electric current value I is equal to 70% of the maximum value Imax of electric current in accordance with this. The moment the electric current value I reaches 70% of the maximum value Imax of electric current, coagulation is considered to be completed, and the set output is reduced to 50% of the set output level.

The electric current value I is measured in step S58 in FIG. 13 when 10 seconds have elapsed following the start of output. In step S59, a comparison is made to determine whether the electric current value I is less than 90% (threshold value) of the maximum value Imax of electric current. If the electric current value I in step S59 is equal to or greater than the threshold value (is equal to or greater than 90% of Imax), the operation returns to step S58, the processes are repeated, and the power output is reduced to 50% of the set output in step S60 when the electric current value I is less than 90% of the maximum value Imax of electric current.

The term "in blood" in FIG. 14 indicates a state in which coagulation is considered to be completed and the power output is reduced to 50% of a set output value when the electric current value I in the blood reaches 90% of the maximum value Imax of electric current. If the electric current is dispersed by blood when the blood is subjected to a coagulation treatment in such a manner, a higher threshold value is established and the electric power is reduced when this threshold value is reached.

FIG. 15 shows the relation between the maximum value Imax of electric current and the electric current value serving as the target value of coagulation completion for reducing the power output.

As can be seen in FIG. 15, no target value can be achieved at less than 0.5 second. 70% of the maximum value Imax of electric current is selected as the target value for the time period equal to or greater than 0.5 second but less than 10 seconds. At 10 seconds or greater, 90% of the maximum value Imax of electric current is selected as the target value, and the output is reduced to 50% of the set output when these values are achieved.

The present embodiment has the following merits.

In the present embodiment, the output of the high frequency electric current varies as described above. Because the conditions for such output variations are determined by the measured values and the output time of electric current values, coagulation completion can be identified in a consistent manner irrespective of the contact area between the electrodes 3 and the tissue, and the tissue can be prevented from carbonizing or adhering to the electrodes 3.

A disadvantage of prior art is that when blood comes into contact with the electrodes 3, the electric current is stabilized and the tissue carbonized. In the present embodiment, however, the conditions for varying the output of the high frequency electric current are determined based on measured values and output times, making it possible to identify coagulation completion in a consistent manner even when the electric current value varies only slightly. An electric current value was used as the measured value in the present embodiment, but the same merits can be obtained by combining voltage, power, phase difference, sample impedance, or other physical measurements or parameters.

A fourth embodiment will now be described.

Figure 16:
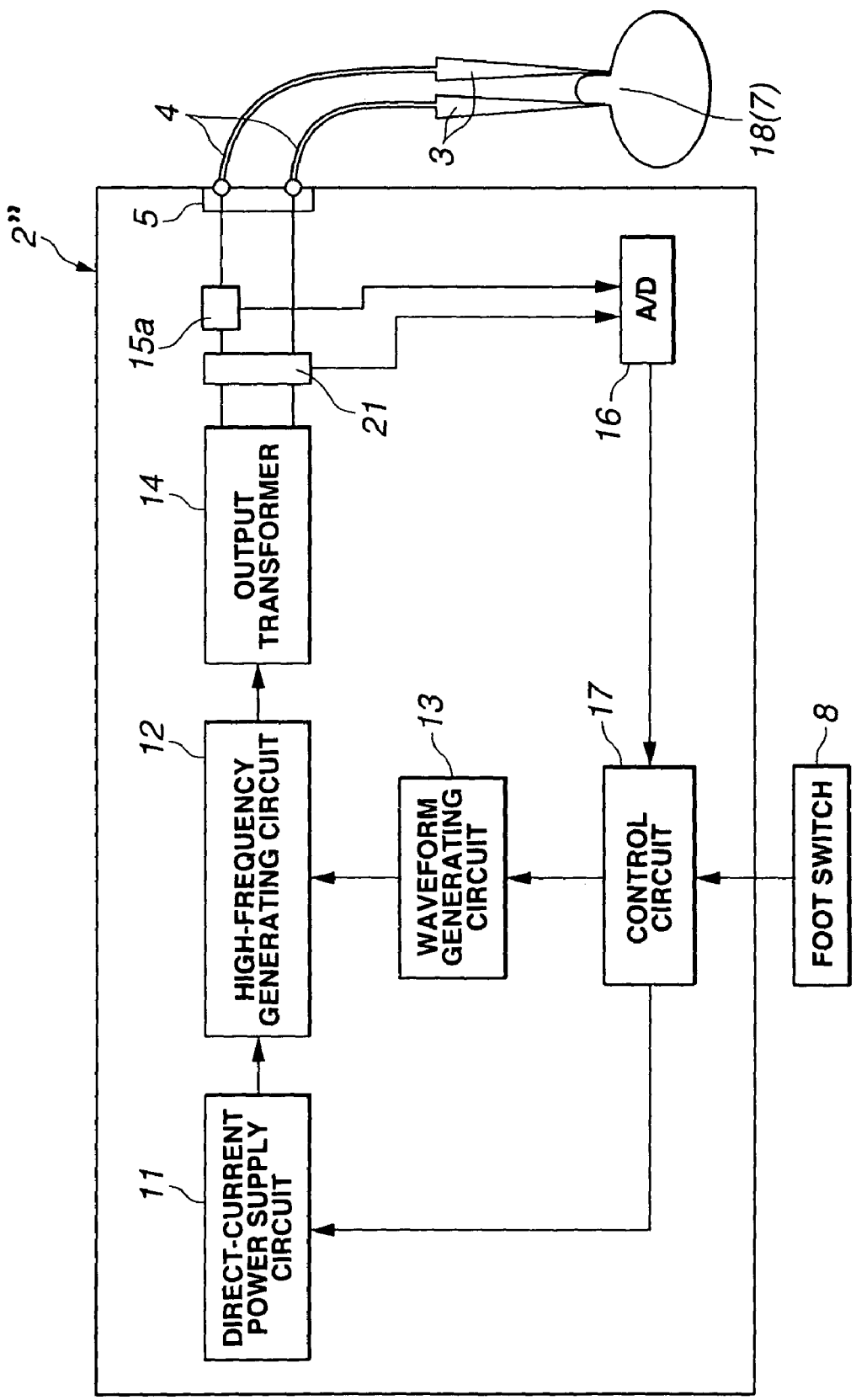
FIG. 16 is a block diagram depicting the structure of a high frequency cauterizing power supply unit pertaining to a fourth embodiment of the present invention.
Figure 17:
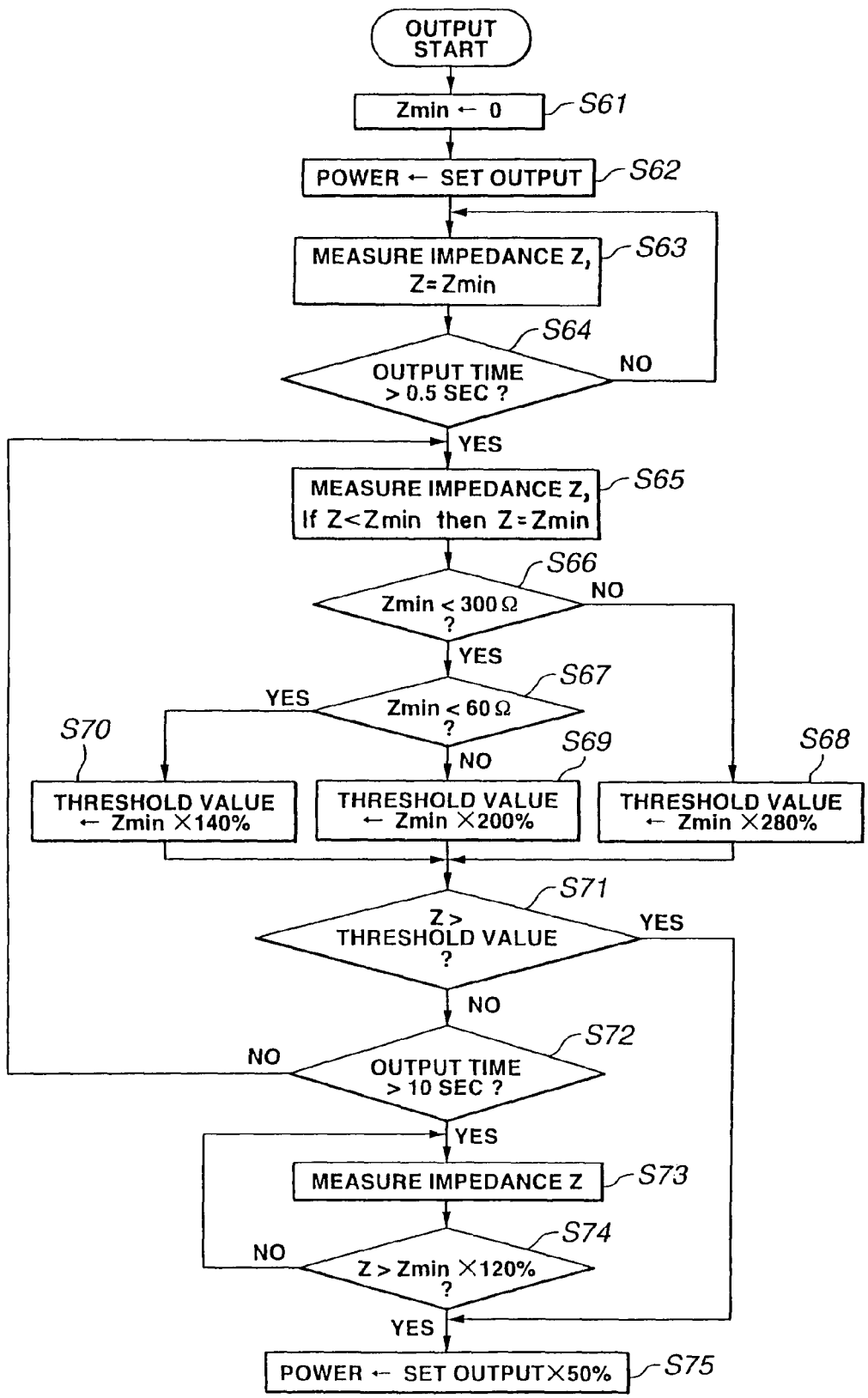
FIG. 17 is a flow chart depicting the control steps of a control circuit.
Figure 18:
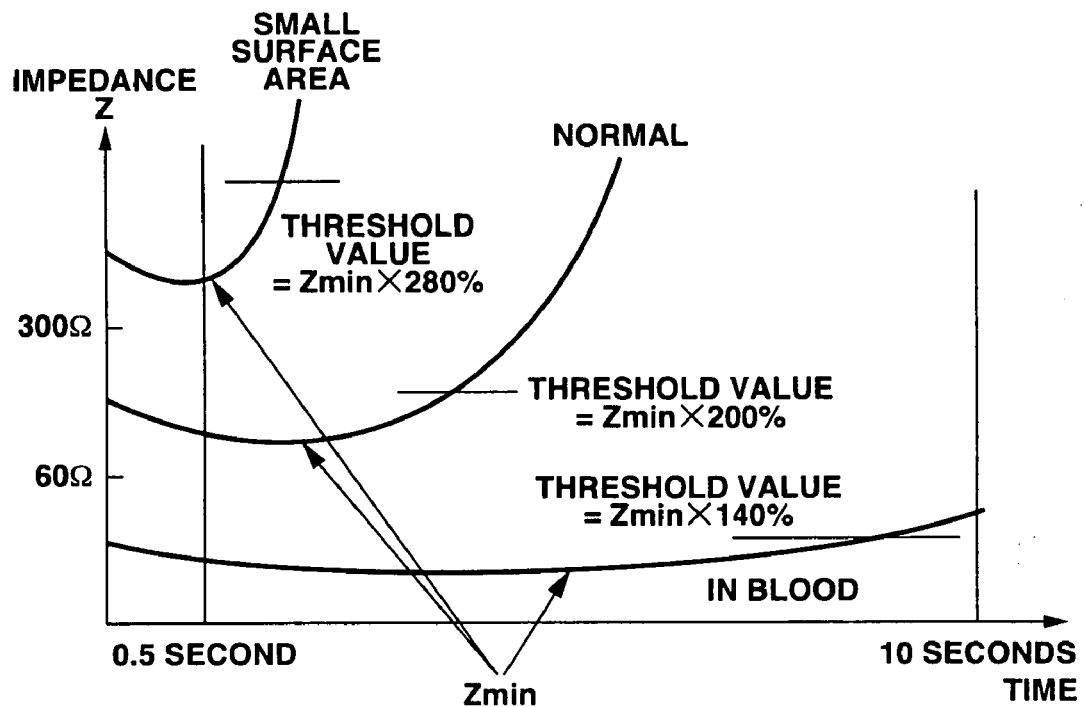
FIG. 18 is an operating diagram depicting the manner in which impedance varies over time in a typical case in which high frequency current is allowed to flow through a biological tissue.
Figure 19:
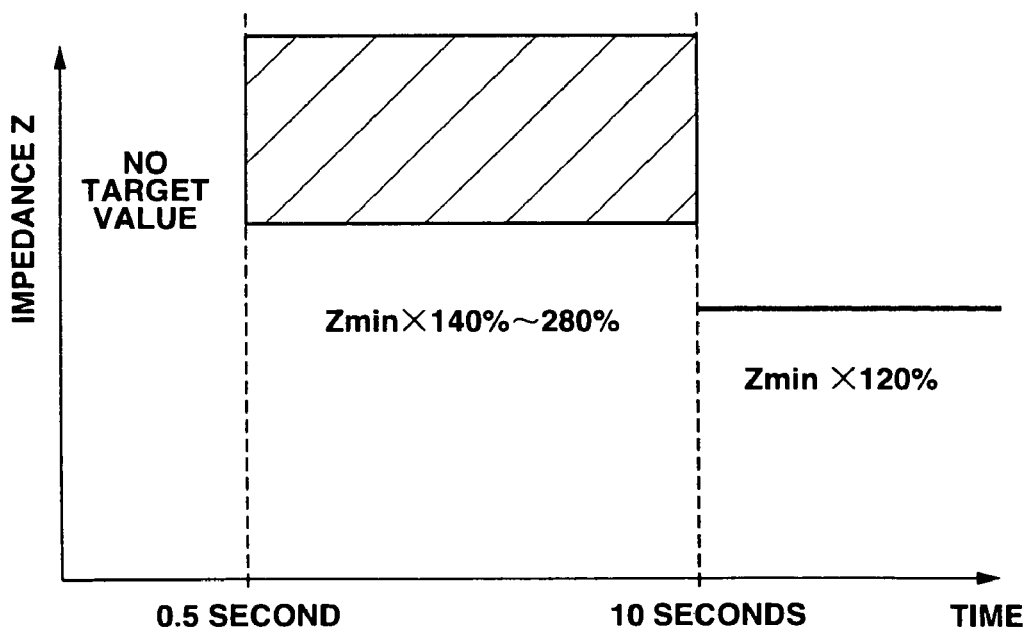
FIG. 19 is a diagram illustrating the impedance threshold value (target value) for reducing the output time and power.
Figure 20:
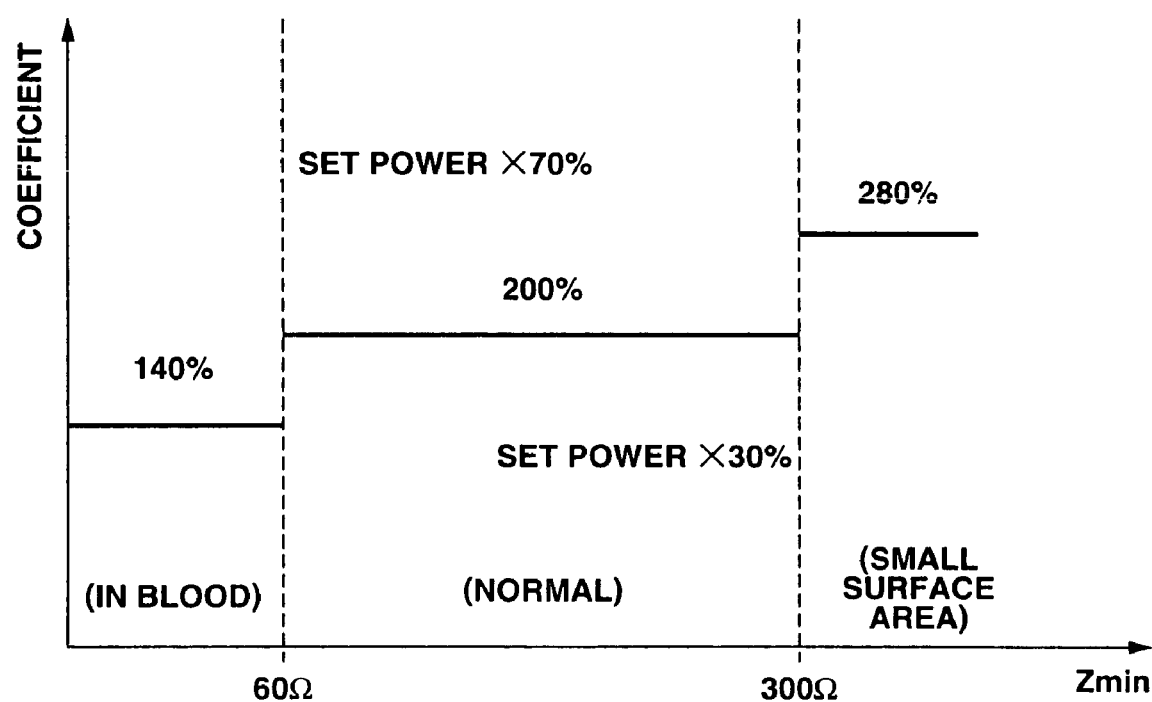
FIG. 20 is a diagram depicting the manner in which the threshold value (target value) coefficient is determined based on minimum impedance value.

The fourth embodiment of the present invention will now be described with reference to FIGS. 16 to 20. FIG. 16 is a block diagram depicting the structure of a high frequency cauterizing power supply unit. FIG. 17 is a flow chart depicting the control steps of the control circuit in FIG. 16. FIG. 18 is an operating diagram depicting the manner in which impedance varies over time in a typical case in which high frequency current is allowed to flow through a biological tissue. FIG. 19 is a diagram illustrating the manner in which the coefficient of a threshold value is determined based on minimum impedance. FIG. 20 is a diagram depicting the manner in which the threshold value coefficient is determined based on minimum impedance value.

The fourth embodiment is substantially similar in structure to the third embodiment. Consequently, the differences alone will be described, identical components will be designated using the same symbols, and their description will be omitted.

The high frequency cauterizing power supply unit 2'' pertaining to this embodiment (FIG. 16) is configured such that the two terminals of an output transformer 14 are provided with a voltage sensor 21 for sensing the voltage therebetween. The signal from the voltage sensor 21 is inputted together with the signal from a current sensor 15a to a control circuit 17 via an A/D converter circuit 16. Other details of the control circuit 17 are the same as in the third embodiment.

The high frequency cauterizing power supply unit 2'' shown in FIG. 16 is configured such that one of the current sensors 15b for the high frequency cauterizing power supply unit 2 shown in FIG. 2 is replaced by a voltage sensor 21.

The third embodiment was configured such that the sampled electric current was measured over time, coagulation completion was confirmed by determining whether a level below a threshold value corresponding to a prescribed proportion of the maximum value Imax of electric current had been achieved, and the high frequency electric current output was monitored. The present embodiment is different in that voltage and electric current are measured, impedance is calculated by dividing the voltage by the current, and the process is monitored to determine whether this value is below (or above) a prescribed impedance minimum (or minimum impedance) Zmin. The aforementioned therapeutic condition is determined based on the time needed to achieve the sampled minimum impedance.

If the measured impedance Z has reached a prescribed value or a prescribed state within a certain range or the like, a threshold value (target value) is established according to this value. The amount of time corresponding to variations in the impedance value is monitored in order to determine whether the impedance Z thus measured is greater than the threshold value used to determine whether coagulation has been completed. Coagulation is considered to be completed at the moment when the impedance value exceeds the threshold value, and the electric power is reduced in a controlled manner.

In all other respects the structure is the same as in the third embodiment.

Operation of the embodiment thus configured will now be described.

The control circuit 17 performs a control routine in accordance with the flow chart shown in FIG. 17. Steps S61 to S64 are substantially the same as in the third embodiment. In the present embodiment, however, impedance Z is measured by dividing a voltage value by an electric current value, and the resulting value is used to control electric power and therapeutic condition sensing. Specifically, 0 is substituted for the minimum impedance Zmin in step S61, the electric power is set to a predetermined set output value in the subsequent step S62, and impedance Z is measured in the subsequent step S63. It is further determined in the subsequent step S64 whether the output time is greater than 0.5 second, the operation returns to step S63 if the result is equal to or less than 0.5 second, and the operation proceeds to the subsequent step S65 and impedance Z is measured if the result is greater than 0.5 second.

Like the second embodiment, it is possible to recognize $Z_{min}$ among the impedance values Z sampled at regular sampling intervals.

Impedance Z is measured in step S65, it is determined in the subsequent step S66 whether the impedance minimum Zmin is less than 300 Ω, and if it is indeed the case, it is determined in the subsequent step S67 whether the impedance minimum Zmin is less than 60 Ω.

If the impedance minimum Zmin is no less than 300 Ω, the threshold value is set to Zmin×280% in step S68. The threshold value is set to Zmin×200% in step S69 if it is concluded in step S67 that the impedance minimum Zmin is no less than 60 Ω. Conversely, the threshold value is set to Zmin×140% if the impedance minimum is less than 60 Ω.

The threshold value (target value) for ascertaining coagulation completion is set in accordance with the range of impedance minimum values Zmin thus measured, it is then determined whether impedance Z exceeds the threshold value in step S71, coagulation is regarded as being completed if this is indeed the case, the operation proceeds to step S75, and the electric power is reduced to 50% of the set output value.

Conversely, it is determined in the subsequent step S72 whether the output time is equal to or greater than 10 seconds if the threshold value is not exceeded, the operation returns to step S65 if the time is equal to or less than 10 seconds, and the same processes are repeated until the time exceeds 10 seconds. The impedance Z of step S73 is measured if the impedance Z fails to exceed the threshold value after 10 seconds have elapsed.

FIG. 18 shows the manner in which impedance Z varies when the impedance minimum Zmin is 60 Ω or less, 60–300 Ω, or 300 Ω or greater. The corresponding threshold values are also shown.

With a small surface area, impedance Z achieves its minimum value Zmin in a short time and increases thereafter with drying. In this case, the threshold value may, for example, be set such that coagulation is regarded as being completed when the level corresponding to 280% of the impedance minimum Zmin is reached. In a standard case (surface area), a lower impedance minimum Zmin is established at a lower rate, and the impedance Z increases thereafter with drying. In this case, the threshold value may, for example, be set such that coagulation is regarded as being completed when the level corresponding to 200% of the impedance minimum Zmin is reached.

High frequency electric current is dispersed more readily in the blood, a lower impedance minimum Zmin is achieved at a lower rate in a longer time than in the case of standard surface area, and the impedance Z then increases with drying. In this case, the threshold value may, for example, be set such that coagulation is regarded as being completed when the level corresponding to 140% of the impedance minimum Zmin is reached.

FIG. 19 shows the relation between the output time and the target value of impedance Z at which the electric power starts decreasing. Specifically, the target value cannot be attained at less than 0.5 second, and a value within a variability range of 140–280% can be set as the target value in accordance with the impedance minimum Zmin thus measured when the time is between 0.5 and 10 seconds. Furthermore, a value corresponding to 120% of the impedance minimum Zmin can be set as the threshold value after more than 10 seconds have elapsed.

FIG. 20 shows the relation between the coefficient of a threshold value (target value) and the impedance minimum Zmin for an output period of 0.5 to 10 seconds. As described above, conditions referred to as "in the blood," "standard surface area of contact," and "reduced surface area of contact" are regarded as having been established when the impedance minima Zmin measured within a period of 0.5 to 10 seconds are 60 Ω or less, 60–300 Ω, and 300 Ω or greater, respectively, indicating that coefficient values corresponding to 140%, 200%, and 280%, respectively, of the impedance minimum Zmin have been set as threshold values (target values).

Impedance Z is measured in step S73, and it is determined in the subsequent step S74 whether the value of impedance Z exceeds Zmin×120%. If impedance Z is no greater than Zmin×120%, the operation returns to step S73, and if this value is not exceeded, the operation proceeds to step S75, and the power output is reduced to 50% of the set output value.

The present embodiment has the following merits.

The merits of the third embodiment are complemented by the fact that because the present embodiment makes it possible to vary the coefficient used to calculate the target value (that is, the threshold value) on the basis of the impedance minimum, it is possible to identify coagulation completion more consistently and to prevent the tissue from carbonizing or adhering to electrodes.

Impedance was used in the present embodiment, but the same merits can be obtained using voltage, power, phase difference, or other physical measurements or parameters.

Modifications of the above-described embodiments also fall within the scope of the present invention. It is, for example, possible to set or otherwise define the threshold value in a more detailed manner during steps S56 to S60 in FIG. 17.

It is also possible to partially combine the above-described embodiments or the like.

In addition, the above embodiments were described with reference to a therapeutic treatment performed in the case of coagulation, but the same can be applied to incision or other types of therapeutic treatment.

As described above, the present invention allows therapeutic treatments to be performed irrespective of the contact area by adopting a routine in which a therapeutic condition is monitored based on variations in high frequency electric current, and the state of output or the like is controlled based on the monitoring results.

Another feature of the present invention is that a therapeutic treatment can be performed irrespective of the contact area by monitoring the therapeutic condition, which is based on the amount of time corresponding to variations in the high frequency electric current, and controlling the output condition or the like on the basis of the monitoring results.

Yet another feature of the present invention is that biological tissue can be prevented from being carbonized or otherwise degraded by monitoring the amount of time corresponding to variations in the electric current output of a high frequency electric current generating circuit, detecting whether coagulation or another therapeutic treatment is completed, and reducing the output of the high frequency electric current generating circuit or performing another control routine upon completion of the therapeutic treatment.

What is claimed is:

1. An electric operation apparatus comprising:
a high frequency electric current generating circuit that generates a high frequency electric current for feeding the high frequency electric current to electrodes;
a direct current power supply circuit that supplies variable direct current electric power to the high frequency electric current generating circuit to adjust an output of the high frequency electric current generating circuit;
a detecting circuit including at least a sensor for monitoring a therapeutic condition brought about by the high frequency electric current during a treatment;
a therapeutic condition estimation circuit that estimates the therapeutic condition based on information of the therapeutic condition monitored during the treatment, the therapeutic condition estimation circuit selecting a target value corresponding to the estimated therapeutic condition upon completion of the treatment among a plurality of predetermined target values, said information being based on dimensions of a contact area between said electrodes and a treatment site; and
a supplied power setting circuit that sets the electric power supplied by the direct current power supply circuit, the supplied power setting circuit reducing the electric power supplied by a predetermined fraction to a predetermined supply condition so as to reduce the high frequency electric current if a detected result of the detecting circuit reaches the target value selected by the therapeutic condition estimation circuit.

2. The electric operation apparatus of claim 1, wherein the therapeutic condition estimation circuit selects the target value based on a maximum of the high frequency electric current value.

3. The electric operation apparatus of claim 1, wherein the target value is determined based on a maximum high frequency electric current value.

4. The electric operation apparatus of claim 1, wherein the therapeutic condition estimation circuit selects the target value based on an amount of time corresponding to variations in a sampled electric current value.

5. The electric operation apparatus of claim 1, wherein the therapeutic condition estimation circuit selects the target value based on a time needed to achieve a maximum sampled electric current value.

6. The electric operation apparatus of claim 5, wherein the supplied power setting circuit compares the current high frequency electric current value detected by the detecting circuit with a threshold value determined based on the maximum value, and modifies the setting such that the supplied power is reduced based on the comparison result.

7. The electric operation apparatus of claim 5, wherein the supplied power setting circuit determines whether the high frequency electric current value reaches a predetermined threshold value after a time period predetermined to indicate that a blood coagulation treatment has been completed, and modifies the setting such that the supplied electric power is reduced if it is confirmed that coagulation has indeed occurred.

8. The electric operation apparatus of claim 1, wherein the therapeutic condition estimation circuit selects the target value based on an amount of time corresponding to variations in a sampled impedance value of a subject being treated.

9. The electric operation apparatus of claim 1, wherein the therapeutic condition estimation circuit selects the target value based on a time needed for a sampled impedance value of a subject being treated to reach a minimum value.

10. The electric operation apparatus of claim 9, wherein the supplied power setting circuit compares the current impedance value with a target value established based on the minimum value, and modifies the setting such that the supplied power is reduced based on the comparison result.

11. The electric operation apparatus of claim 9, wherein the supplied power setting circuit determines whether the impedance value reaches a predetermined threshold value after a time period predetermined to indicate that a blood coagulation treatment has been completed, and modifies the setting such that the supplied electric power is reduced if it is confirmed that coagulation has indeed occurred.

12. An output control method for an electric operation apparatus comprising a high frequency electric current generating circuit that generates a high frequency electric current for feeding the high frequency electric current to electrodes, a direct current power supply circuit that supplies variable direct current electric power to the high frequency electric current generating circuit to adjust an output of the high frequency electric current generating circuit, and a detecting circuit that monitors a therapeutic condition brought about by the high frequency electric current during a treatment, the method comprising:

monitoring the therapeutic condition brought about by the high frequency electric current during the treatment;

estimating the therapeutic condition upon completion of the treatment based on information of the therapeutic condition monitored during the treatment, said information being based on dimensions of a contact area between said electrodes and a treatment site;

setting a target value based on an estimated result obtained at the estimating step; and rendering the direct current power supply circuit a predetermined supply condition in order to reduce a supply power of the direct current power supply circuit by a predetermined fraction if a detected result reaches the target value set at the setting step.

13. An electric operation apparatus comprising:

a high frequency electric current generating circuit that generates a high frequency electric current for feeding the high frequency electric current to electrodes;

a direct current power supply circuit that supplies variable direct current electric power to the high frequency electric current generating circuit to adjust an output of the high frequency electric current generating circuit;

a detecting circuit including at least a sensor for monitoring a therapeutic condition brought about by the high frequency electric current during a treatment;

a therapeutic condition estimation circuit that estimates the therapeutic condition based on information of the therapeutic condition monitored during the treatment, the therapeutic condition estimation circuit selecting a target value corresponding to the estimated therapeutic condition upon completion of the treatment among a plurality of predetermined target values; and a supplied power setting circuit that sets the electric power supplied by the direct current power supply circuit, the supplied power setting circuit changing the electric power supplied to a predetermined supply condition so as to reduce the high frequency electric current if a detected result of the detecting circuit reaches a target value set by the therapeutic condition estimation circuit;

wherein the therapeutic condition estimation circuit selects the target value based on a time needed to achieve a maximum sampled electric current value.

14. The electric operation apparatus of claim 13, wherein the supplied power setting circuit compares the current high frequency electric current value detected by the detecting circuit with a threshold value determined based on the maximum value, and modifies the setting such that the supplied power is reduced based on the comparison result.

15. The electric operation apparatus of claim 13, wherein the supplied power setting circuit determines whether the high frequency electric current value reaches a predetermined threshold value after a time period predetermined to indicate that a blood coagulation treatment has been completed, and modifies the setting such that the supplied electric power is reduced if it is confirmed that coagulation has indeed occurred.

16. The electric operation apparatus of claim 13, wherein the therapeutic condition estimation circuit selects the target value based on a maximum of the high frequency electric current value.

17. The electric operation apparatus of claim 13, wherein the target value is determined based on a maximum high frequency electric current value.

18. The electric operation apparatus of claim 13, wherein the therapeutic condition estimation circuit selects the target value based on an amount of time corresponding to variations in a sampled electric current value.

19. The electric operation apparatus of claim 13, wherein the therapeutic condition estimation circuit selects the target value based on an amount of time corresponding to variations in a sampled impedance value of a subject being treated.

20. An electric operation apparatus comprising:

a high frequency electric current generating circuit that generates a high frequency electric current for feeding the high frequency electric current to electrodes;

a direct current power supply circuit that supplies variable direct current electric power to the high frequency electric current generating circuit to adjust an output of the high frequency electric current generating circuit;

a detecting circuit including at least a sensor for monitoring a therapeutic condition brought about by the high frequency electric current during a treatment;

a therapeutic condition estimation circuit that estimates the therapeutic condition based on information of the therapeutic condition monitored during the treatment, the therapeutic condition estimation circuit selecting a target value corresponding to the estimated therapeutic condition upon completion of the treatment among a plurality of predetermined target values; and a supplied power setting circuit that sets the electric power supplied by the direct current power supply circuit, the supplied power setting circuit changing the electric power supplied to a predetermined supply condition so as to reduce the high frequency electric current if a detected result of the detecting circuit reaches a target value set by the therapeutic condition estimation circuit;

wherein the therapeutic condition estimation circuit selects the target value based on a time needed for a sampled impedance value of a subject being treated to reach a minimum value.

21. The electric operation apparatus of claim 20, wherein the supplied power setting circuit compares the current impedance value with a target value established based on the minimum value, and modifies the setting such that the supplied power is reduced based on the comparison result.

22. The electric operation apparatus of claim 20, wherein the supplied power setting circuit determines whether the impedance value reaches a predetermined threshold value after a time period predetermined to indicate that a blood coagulation treatment has been completed, and modifies the setting such that the supplied electric power is reduced if it is confirmed that coagulation has indeed occurred.

23. The electric operation apparatus of claim 20, wherein the therapeutic condition estimation circuit selects the target value based on a maximum of the high frequency electric current value.

24. The electric operation apparatus of claim 20, wherein the target value is determined based on a maximum high frequency electric current value.

25. The electric operation apparatus of claim 20, wherein the therapeutic condition estimation circuit selects the target value based on an amount of time corresponding to variations in a sampled electric current value.

26. The electric operation apparatus of claim 20, wherein the therapeutic condition estimation circuit selects the target value based on an amount of time corresponding to variations in a sampled impedance value of a subject being treated.

27. An output control method for an electric operation apparatus comprising a high frequency electric current generating circuit that generates a high frequency electric current for feeding the high frequency electric current to electrodes, a direct current power supply circuit that supplies variable direct current electric power to the high frequency electric current generating circuit to adjust an output of the high frequency electric current generating circuit, and a detecting circuit that monitors a therapeutic condition brought about by the high frequency electric current during a treatment, the method comprising:

monitoring the therapeutic condition brought about by the high frequency electric current during the treatment;

estimating the therapeutic condition upon completion of the treatment based on information of the therapeutic condition monitored during the treatment;

setting a target value based on an estimated result obtained at the estimating step, and based on a time needed to achieve a maximum sampled electric current value; and rendering the direct current power supply circuit a predetermined supply condition in order to reduce a supply power of the direct current power supply circuit if a detected result reaches the target value set at the setting step.

28. An output control method for an electric operation apparatus comprising a high frequency electric current generating circuit that generates a high frequency electric current for feeding the high frequency electric current to electrodes, a direct current power supply circuit that supplies variable direct current electric power to the high frequency electric current generating circuit to adjust an output of the high frequency electric current generating circuit, and a detecting circuit that monitors a therapeutic condition brought about by the high frequency electric current during a treatment, the method comprising:

monitoring the therapeutic condition brought about by the high frequency electric current during the treatment;

estimating the therapeutic condition upon completion of the treatment based on information of the therapeutic condition monitored during the treatment;

setting a target value based on an estimated result obtained at the estimating step, and based on a time needed for a sampled impedance value of a subject being treated to reach a minimum value; and rendering the direct current power supply circuit a predetermined supply condition in order to reduce a supply power of the direct current power supply circuit if a detected result reaches the target value set at the setting step.

* * * * *